United States Patent
Ho et al.

(10) Patent No.: US 9,029,326 B2
(45) Date of Patent: May 12, 2015

(54) POLYPEPTIDES, NUCLEIC ACID MOLECULE ENCODING POLYPEPTIDES, AND USES OF POLYPEPTIDES

(71) Applicant: China Medical University, Taichung (TW)

(72) Inventors: Tin-Yun Ho, Taichung (TW); Chien-Yun Hsiang, Taichung (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 14/160,791

(22) Filed: Jan. 22, 2014

(65) Prior Publication Data

US 2014/0155323 A1    Jun. 5, 2014

Related U.S. Application Data

(62) Division of application No. 13/557,374, filed on Jul. 25, 2012, now Pat. No. 8,697,649.

(30) Foreign Application Priority Data

May 18, 2012 (TW) .............................. 101117779 A

(51) Int. Cl.
| | | |
|---|---|---|
| C07K 7/08 | (2006.01) | |
| A61K 38/10 | (2006.01) | |
| C07K 7/06 | (2006.01) | |
| C07K 14/415 | (2006.01) | |
| A61K 38/00 | (2006.01) | |

(52) U.S. Cl.
CPC .................. *A61K 38/10* (2013.01); *A61K 38/00* (2013.01); *C07K 7/06* (2013.01); *C07K 7/08* (2013.01); *C07K 14/415* (2013.01)

(58) Field of Classification Search
None
See application file for complete search history.

(56) References Cited

U.S. PATENT DOCUMENTS

| 6,127,338 A | 10/2000 | Nag et al. |
|---|---|---|
| 7,393,919 B2 | 7/2008 | Levetan et al. |
| 8,697,649 B2 * | 4/2014 | Ho et al. ..................... 514/13.1 |
| 2006/0217300 A1 | 9/2006 | Dong |
| 2010/0137220 A1 | 6/2010 | Ho et al. |
| 2011/0212892 A1 | 9/2011 | Nagamine |
| 2013/0004596 A1 | 1/2013 | Chung et al. |
| 2013/0184272 A1 | 7/2013 | Oka et al. |

FOREIGN PATENT DOCUMENTS

| JP | 2010124827 A | 6/2010 |
|---|---|---|
| JP | 2011254743 A | 12/2011 |
| TW | I283684 | 2/2004 |
| WO | 2010050422 A1 | 5/2010 |
| WO | 2011064352 A1 | 6/2011 |
| WO | 2011102690 A2 | 8/2011 |
| WO | 2012010966 A2 | 1/2012 |
| WO | 2012036293 A1 | 3/2012 |

OTHER PUBLICATIONS

Choi, S.B. et al., The insulin sensitizing effect of homoisoflavone-enriched fraction in *Liriope platyphylla* Wang et Tang via PI3-kinase pathway, Life Sciences 2004;75:2653-2664.

Cheng, W-Y. et al., Comprehensive evaluation of a novel nuclear factor-κB inhibitor, quinoclamine, by transcriptomic analysis. 2009; Brit. J. Pharmacol., 157(5): 746-756.

Cheng, H.M. et al., Application of bioactivity database of Chinese herbal medicine on the therapeutic prediction, drug development, and safety evaluation. 2010; J. Ethnopharmacol. 132 (2): 429-437.

Hsiang, C.Y. et al., Nuclear factor-κB bioluminescence imaging-guided transcriptomic analysis for the assessment of host-biomaterial interaction in vivo. 2009; Biomaterials 30 (17): 3042-3049.

* cited by examiner

*Primary Examiner* — Karlheinz R Skowronek
*Assistant Examiner* — Mindy Newman
(74) *Attorney, Agent, or Firm* — Michael W. Ferrell; Ferrells, PLLC; Anna L. Kinney

(57) ABSTRACT

A polypeptide, a nucleic acid molecule encoding the polypeptide and a pharmaceutical composition comprising the polypeptide are provided. The polypeptide is as defined in the description, can bind to insulin receptors, and is effective in reducing blood sugar, reducing glycated hemoglobin, and ameliorating hepato-renal disorders caused by diabetes.

6 Claims, 4 Drawing Sheets
(2 of 4 Drawing Sheet(s) Filed in Color)

though there are a lot of pharmaceuti-

SEQUENCE LISTING

<160> NUMBER OF SEQ ID NOS: 364

<210> SEQ ID NO 1
<211> LENGTH: 68
<212> TYPE: PRT
<213> ORGANISM: Momordica charantia

<400> SEQUENCE: 1

Ser Arg Cys Gln Gly Lys Ser Ser Trp Pro Gln Leu Val Gly Ser Thr
1               5                   10                  15

Gly Ala Ala Ala Lys Ala Val Ile Glu Arg Glu Asn Pro Arg Val Arg
            20                  25                  30

Ala Val Ile Ile Lys Val Gly Ser Gly Ala Thr Lys Asp Phe Arg Cys
        35                  40                  45

Asp Arg Val Arg Val Trp Val Thr Glu Arg Gly Ile Val Ala Arg Pro
    50                  55                  60

Pro Thr Ile Gly
65

<210> SEQ ID NO 2
<211> LENGTH: 19
<212> TYPE: PRT
<213> ORGANISM: Momordica charantia

<400> SEQUENCE: 2

Ser Arg Cys Gln Gly Lys Ser Ser Trp Pro Gly Leu Val Gly Ser Thr
1               5                   10                  15

Gly Ala Ala

<210> SEQ ID NO 3
<211> LENGTH: 18
<212> TYPE: PRT
<213> ORGANISM: Momordica charantia

<400> SEQUENCE: 3

Gly Ala Ala Ala Lys Ala Val Ile Glu Arg Glu Asn Pro Arg Val Arg
1               5                   10                  15

Val Ile

<210> SEQ ID NO 4
<211> LENGTH: 19
<212> TYPE: PRT
<213> ORGANISM: Momordica charantia

<400> SEQUENCE: 4

Val Ile Ile Lys Val Gly Ser Gly Ala Thr Lys Asp Phe Arg Cys Asp
1               5                   10                  15

Arg Val Arg

<210> SEQ ID NO 5
<211> LENGTH: 24
<212> TYPE: PRT
<213> ORGANISM: Momordica charantia

<400> SEQUENCE: 5

Asp Phe Arg Cys Asp Arg Val Arg Val Trp Val Thr Glu Arg Gly Ile
1               5                   10                  15

Val Ala Arg Pro Pro Thr Ile Gly
            20

<210> SEQ ID NO 6
<211> LENGTH: 19
<212> TYPE: PRT
<213> ORGANISM: Momordica charantia

<400> SEQUENCE: 6

```
Arg Val Arg Val Trp Val Thr Glu Arg Gly Ile Val Ala Arg Pro Pro
1               5                   10                  15

Thr Ile Gly

<210> SEQ ID NO 7
<211> LENGTH: 9
<212> TYPE: PRT
<213> ORGANISM: Momordica charantia

<400> SEQUENCE: 7

Ile Val Ala Arg Pro Pro Thr Ile Gly
1               5

<210> SEQ ID NO 8
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 8

Arg Val Ala Arg Pro Pro Thr Ile Gly
1               5

<210> SEQ ID NO 9
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 9

Ile Arg Ala Arg Pro Pro Thr Ile Gly
1               5

<210> SEQ ID NO 10
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 10

Ile Val Arg Arg Pro Pro Thr Ile Gly
1               5

<210> SEQ ID NO 11
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 11

Ile Val Ala Arg Arg Pro Thr Ile Gly
1               5

<210> SEQ ID NO 12
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 12

Ile Val Ala Arg Pro Arg Thr Ile Gly
```

```
<210> SEQ ID NO 13
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 13

Ile Val Ala Arg Pro Pro Arg Ile Gly
1               5

<210> SEQ ID NO 14
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 14

Ile Val Ala Arg Pro Pro Thr Arg Gly
1               5

<210> SEQ ID NO 15
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 15

Ile Val Ala Arg Pro Pro Thr Ile Arg
1               5

<210> SEQ ID NO 16
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 16

Ala Val Ala Arg Pro Pro Thr Ile Gly
1               5

<210> SEQ ID NO 17
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 17

Ile Ala Ala Arg Pro Pro Thr Ile Gly
1               5

<210> SEQ ID NO 18
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 18

Ile Val Ala Ala Pro Pro Thr Ile Gly
1               5
```

```
<210> SEQ ID NO 19
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 19

Ile Val Ala Arg Ala Pro Thr Ile Gly
1               5

<210> SEQ ID NO 20
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 20

Ile Val Ala Arg Pro Ala Thr Ile Gly
1               5

<210> SEQ ID NO 21
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 21

Ile Val Ala Arg Pro Pro Ala Ile Gly
1               5

<210> SEQ ID NO 22
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 22

Ile Val Ala Arg Pro Pro Thr Ala Gly
1               5

<210> SEQ ID NO 23
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 23

Ile Val Ala Arg Pro Pro Thr Ile Ala
1               5

<210> SEQ ID NO 24
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 24

Val Val Ala Arg Pro Pro Thr Ile Gly
1               5
```

<210> SEQ ID NO 25
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 25

Ile Val Val Arg Pro Pro Thr Ile Gly
1               5

<210> SEQ ID NO 26
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 26

Ile Val Ala Val Pro Pro Thr Ile Gly
1               5

<210> SEQ ID NO 27
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 27

Ile Val Ala Arg Val Pro Thr Ile Gly
1               5

<210> SEQ ID NO 28
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 28

Ile Val Ala Arg Pro Val Thr Ile Gly
1               5

<210> SEQ ID NO 29
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 29

Ile Val Ala Arg Pro Pro Val Ile Gly
1               5

<210> SEQ ID NO 30
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 30

Ile Val Ala Arg Pro Pro Thr Val Gly
1               5

```
<210> SEQ ID NO 31
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 31

Ile Val Ala Arg Pro Pro Thr Ile Val
1               5

<210> SEQ ID NO 32
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 32

Phe Val Ala Arg Pro Pro Thr Ile Gly
1               5

<210> SEQ ID NO 33
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 33

Ile Phe Ala Arg Pro Pro Thr Ile Gly
1               5

<210> SEQ ID NO 34
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 34

Ile Val Phe Arg Pro Pro Thr Ile Gly
1               5

<210> SEQ ID NO 35
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 35

Ile Val Ala Phe Pro Pro Thr Ile Gly
1               5

<210> SEQ ID NO 36
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 36

Ile Val Ala Arg Phe Pro Thr Ile Gly
1               5

<210> SEQ ID NO 37
```

```
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 37

Ile Val Ala Arg Pro Phe Thr Ile Gly
1               5

<210> SEQ ID NO 38
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 38

Ile Val Ala Arg Pro Pro Phe Ile Gly
1               5

<210> SEQ ID NO 39
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 39

Ile Val Ala Arg Pro Pro Thr Phe Gly
1               5

<210> SEQ ID NO 40
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 40

Ile Val Ala Arg Pro Pro Thr Ile Phe
1               5

<210> SEQ ID NO 41
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 41

Pro Val Ala Arg Pro Pro Thr Ile Gly
1               5

<210> SEQ ID NO 42
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 42

Ile Pro Ala Arg Pro Pro Thr Ile Gly
1               5

<210> SEQ ID NO 43
<211> LENGTH: 9
```

```
<212> TYPE: PRT
<213> ORGANISM: Artificial sequence
<220> FEATURE:
<223> OTHER INFORMATION: homologues of SEQ ID NO:1

<400> SEQUENCE: 43

Ile Val Pro Arg Pro Pro Thr Ile Gly
1               5

<210> SEQ ID NO 44
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 44

Ile Val Ala Pro Pro Pro Thr Ile Gly
1               5

<210> SEQ ID NO 45
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 45

Ile Val Ala Arg Pro Pro Pro Ile Gly
1               5

<210> SEQ ID NO 46
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 46

Ile Val Ala Arg Pro Pro Thr Pro Gly
1               5

<210> SEQ ID NO 47
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 47

Ile Val Ala Arg Pro Pro Thr Ile Pro
1               5

<210> SEQ ID NO 48
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 48

Met Val Ala Arg Pro Pro Thr Ile Gly
1               5

<210> SEQ ID NO 49
<211> LENGTH: 9
<212> TYPE: PRT
```

```
<213> ORGANISM: Artificial sequence
<220> FEATURE:
<223> OTHER INFORMATION: homologues of SEQ ID NO:1

<400> SEQUENCE: 49

Ile Met Ala Arg Pro Pro Thr Ile Gly
1               5

<210> SEQ ID NO 50
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 50

Ile Val Met Arg Pro Pro Thr Ile Gly
1               5

<210> SEQ ID NO 51
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 51

Ile Val Ala Met Pro Pro Thr Ile Gly
1               5

<210> SEQ ID NO 52
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 52

Ile Val Ala Arg Met Pro Thr Ile Gly
1               5

<210> SEQ ID NO 53
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 53

Ile Val Ala Arg Pro Met Thr Ile Gly
1               5

<210> SEQ ID NO 54
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 54

Ile Val Ala Arg Pro Pro Met Ile Gly
1               5

<210> SEQ ID NO 55
<211> LENGTH: 9
<212> TYPE: PRT
<213> ORGANISM: Artificial sequence
```

-continued

```
<220> FEATURE:
<223> OTHER INFORMATION: homologues of SEQ ID NO:1

<400> SEQUENCE: 55

Ile Val Ala Arg Pro Pro Thr Met Gly
1               5

<210> SEQ ID NO 56
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 56

Ile Val Ala Arg Pro Pro Thr Ile Met
1               5

<210> SEQ ID NO 57
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 57

Ile Ile Ala Arg Pro Pro Thr Ile Gly
1               5

<210> SEQ ID NO 58
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 58

Ile Val Ile Arg Pro Pro Thr Ile Gly
1               5

<210> SEQ ID NO 59
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 59

Ile Val Ala Ile Pro Pro Thr Ile Gly
1               5

<210> SEQ ID NO 60
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 60

Ile Val Ala Arg Ile Pro Thr Ile Gly
1               5

<210> SEQ ID NO 61
<211> LENGTH: 9
<212> TYPE: PRT
<213> ORGANISM: Artificial sequence
<220> FEATURE:
```

<223> OTHER INFORMATION: homologues of SEQ ID NO:1

<400> SEQUENCE: 61

Ile Val Ala Arg Pro Ile Thr Ile Gly
1               5

<210> SEQ ID NO 62
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 62

Ile Val Ala Arg Pro Pro Ile Ile Gly
1               5

<210> SEQ ID NO 63
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 63

Ile Val Ala Arg Pro Pro Thr Ile Ile
1               5

<210> SEQ ID NO 64
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 64

Leu Val Ala Arg Pro Pro Thr Ile Gly
1               5

<210> SEQ ID NO 65
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 65

Ile Leu Ala Arg Pro Pro Thr Ile Gly
1               5

<210> SEQ ID NO 66
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 66

Ile Val Leu Arg Pro Pro Thr Ile Gly
1               5

<210> SEQ ID NO 67
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 67

Ile Val Ala Leu Pro Pro Thr Ile Gly
1               5

<210> SEQ ID NO 68
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 68

Ile Val Ala Arg Leu Pro Thr Ile Gly
1               5

<210> SEQ ID NO 69
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 69

Ile Val Ala Arg Pro Leu Thr Ile Gly
1               5

<210> SEQ ID NO 70
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 70

Ile Val Ala Arg Pro Pro Leu Ile Gly
1               5

<210> SEQ ID NO 71
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 71

Ile Val Ala Arg Pro Pro Thr Leu Gly
1               5

<210> SEQ ID NO 72
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 72

Ile Val Ala Arg Pro Pro Thr Ile Leu
1               5

<210> SEQ ID NO 73
<211> LENGTH: 9
<212> TYPE: PRT
<213> ORGANISM: Artificial sequence
<220> FEATURE:
<223> OTHER INFORMATION: homologues of SEQ ID NO:1

```
<400> SEQUENCE: 73

Asp Val Ala Arg Pro Pro Thr Ile Gly
1               5

<210> SEQ ID NO 74
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 74

Ile Asp Ala Arg Pro Pro Thr Ile Gly
1               5

<210> SEQ ID NO 75
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 75

Ile Val Asp Arg Pro Pro Thr Ile Gly
1               5

<210> SEQ ID NO 76
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 76

Ile Val Ala Asp Pro Pro Thr Ile Gly
1               5

<210> SEQ ID NO 77
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 77

Ile Val Ala Arg Asp Pro Thr Ile Gly
1               5

<210> SEQ ID NO 78
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 78

Ile Val Ala Arg Pro Asp Thr Ile Gly
1               5

<210> SEQ ID NO 79
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 79
```

```
Ile Val Ala Arg Pro Pro Asp Ile Gly
1               5
```

<210> SEQ ID NO 80
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 80

```
Ile Val Ala Arg Pro Pro Thr Asp Gly
1               5
```

<210> SEQ ID NO 81
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 81

```
Ile Val Ala Arg Pro Pro Thr Ile Asp
1               5
```

<210> SEQ ID NO 82
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 82

```
Glu Val Ala Arg Pro Pro Thr Ile Gly
1               5
```

<210> SEQ ID NO 83
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 83

```
Ile Glu Ala Arg Pro Pro Thr Ile Gly
1               5
```

<210> SEQ ID NO 84
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 84

```
Ile Val Glu Arg Pro Pro Thr Ile Gly
1               5
```

<210> SEQ ID NO 85
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 85

```
Ile Val Ala Glu Pro Pro Thr Ile Gly
1               5

<210> SEQ ID NO 86
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 86

Ile Val Ala Arg Glu Pro Thr Ile Gly
1               5

<210> SEQ ID NO 87
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 87

Ile Val Ala Arg Pro Glu Thr Ile Gly
1               5

<210> SEQ ID NO 88
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 88

Ile Val Ala Arg Pro Pro Glu Ile Gly
1               5

<210> SEQ ID NO 89
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 89

Ile Val Ala Arg Pro Pro Thr Glu Gly
1               5

<210> SEQ ID NO 90
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 90

Ile Val Ala Arg Pro Pro Thr Ile Glu
1               5

<210> SEQ ID NO 91
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 91

Lys Val Ala Arg Pro Pro Thr Ile Gly
```

```
1               5
```

<210> SEQ ID NO 92
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 92

```
Ile Lys Ala Arg Pro Pro Thr Ile Gly
1               5
```

<210> SEQ ID NO 93
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 93

```
Ile Val Lys Arg Pro Pro Thr Ile Gly
1               5
```

<210> SEQ ID NO 94
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 94

```
Ile Val Ala Lys Pro Pro Thr Ile Gly
1               5
```

<210> SEQ ID NO 95
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 95

```
Ile Val Ala Arg Lys Pro Thr Ile Gly
1               5
```

<210> SEQ ID NO 96
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 96

```
Ile Val Ala Arg Pro Lys Thr Ile Gly
1               5
```

<210> SEQ ID NO 97
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 97

```
Ile Val Ala Arg Pro Pro Lys Ile Gly
1               5
```

```
<210> SEQ ID NO 98
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 98

Ile Val Ala Arg Pro Pro Thr Lys Gly
1               5

<210> SEQ ID NO 99
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 99

Ile Val Ala Arg Pro Pro Thr Ile Lys
1               5

<210> SEQ ID NO 100
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 100

Gly Val Ala Arg Pro Pro Thr Ile Gly
1               5

<210> SEQ ID NO 101
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 101

Ile Gly Ala Arg Pro Pro Thr Ile Gly
1               5

<210> SEQ ID NO 102
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 102

Ile Val Gly Arg Pro Pro Thr Ile Gly
1               5

<210> SEQ ID NO 103
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 103

Ile Val Ala Gly Pro Pro Thr Ile Gly
1               5
```

<210> SEQ ID NO 104
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 104

Ile Val Ala Arg Gly Pro Thr Ile Gly
1               5

<210> SEQ ID NO 105
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 105

Ile Val Ala Arg Pro Gly Thr Ile Gly
1               5

<210> SEQ ID NO 106
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 106

Ile Val Ala Arg Pro Pro Gly Ile Gly
1               5

<210> SEQ ID NO 107
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 107

Ile Val Ala Arg Pro Pro Thr Gly Gly
1               5

<210> SEQ ID NO 108
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 108

Ser Val Ala Arg Pro Pro Thr Ile Gly
1               5

<210> SEQ ID NO 109
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 109

Ile Ser Ala Arg Pro Pro Thr Ile Gly
1               5

```
<210> SEQ ID NO 110
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 110

Ile Val Ser Arg Pro Pro Thr Ile Gly
1               5

<210> SEQ ID NO 111
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 111

Ile Val Ala Ser Pro Pro Thr Ile Gly
1               5

<210> SEQ ID NO 112
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 112

Ile Val Ala Arg Ser Pro Thr Ile Gly
1               5

<210> SEQ ID NO 113
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 113

Ile Val Ala Arg Pro Ser Thr Ile Gly
1               5

<210> SEQ ID NO 114
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 114

Ile Val Ala Arg Pro Pro Ser Ile Gly
1               5

<210> SEQ ID NO 115
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 115

Ile Val Ala Arg Pro Pro Thr Ser Gly
1               5

<210> SEQ ID NO 116
```

```
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 116

Ile Val Ala Arg Pro Pro Thr Ile Ser
1               5

<210> SEQ ID NO 117
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 117

Thr Val Ala Arg Pro Pro Thr Ile Gly
1               5

<210> SEQ ID NO 118
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 118

Ile Thr Ala Arg Pro Pro Thr Ile Gly
1               5

<210> SEQ ID NO 119
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 119

Ile Val Thr Arg Pro Pro Thr Ile Gly
1               5

<210> SEQ ID NO 120
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 120

Ile Val Ala Thr Pro Pro Thr Ile Gly
1               5

<210> SEQ ID NO 121
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 121

Ile Val Ala Arg Thr Pro Thr Ile Gly
1               5

<210> SEQ ID NO 122
<211> LENGTH: 9
```

```
<212> TYPE: PRT
<213> ORGANISM: Artificial sequence
<220> FEATURE:
<223> OTHER INFORMATION: homologues of SEQ ID NO:1

<400> SEQUENCE: 122

Ile Val Ala Arg Pro Thr Thr Ile Gly
1               5

<210> SEQ ID NO 123
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 123

Ile Val Ala Arg Pro Pro Thr Thr Gly
1               5

<210> SEQ ID NO 124
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 124

Ile Val Ala Arg Pro Pro Thr Ile Thr
1               5

<210> SEQ ID NO 125
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 125

Tyr Val Ala Arg Pro Pro Thr Ile Gly
1               5

<210> SEQ ID NO 126
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 126

Ile Tyr Ala Arg Pro Pro Thr Ile Gly
1               5

<210> SEQ ID NO 127
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 127

Ile Val Tyr Arg Pro Pro Thr Ile Gly
1               5

<210> SEQ ID NO 128
<211> LENGTH: 9
<212> TYPE: PRT
```

<213> ORGANISM: Artificial sequence
<220> FEATURE:
<223> OTHER INFORMATION: homologues of SEQ ID NO:1

<400> SEQUENCE: 128

Ile Val Ala Tyr Pro Pro Thr Ile Gly
1               5

<210> SEQ ID NO 129
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 129

Ile Val Ala Arg Tyr Pro Thr Ile Gly
1               5

<210> SEQ ID NO 130
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 130

Ile Val Ala Arg Pro Tyr Thr Ile Gly
1               5

<210> SEQ ID NO 131
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 131

Ile Val Ala Arg Pro Pro Tyr Ile Gly
1               5

<210> SEQ ID NO 132
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 132

Ile Val Ala Arg Pro Pro Thr Tyr Gly
1               5

<210> SEQ ID NO 133
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 133

Ile Val Ala Arg Pro Pro Thr Ile Tyr
1               5

<210> SEQ ID NO 134
<211> LENGTH: 9
<212> TYPE: PRT
<213> ORGANISM: Artificial sequence

```
<220> FEATURE:
<223> OTHER INFORMATION: homologues of SEQ ID NO:1

<400> SEQUENCE: 134

His Val Ala Arg Pro Pro Thr Ile Gly
 1               5

<210> SEQ ID NO 135
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 135

Ile His Ala Arg Pro Pro Thr Ile Gly
 1               5

<210> SEQ ID NO 136
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 136

Ile Val His Arg Pro Pro Thr Ile Gly
 1               5

<210> SEQ ID NO 137
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 137

Ile Val Ala His Pro Pro Thr Ile Gly
 1               5

<210> SEQ ID NO 138
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 138

Ile Val Ala Arg His Pro Thr Ile Gly
 1               5

<210> SEQ ID NO 139
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 139

Ile Val Ala Arg Pro His Thr Ile Gly
 1               5

<210> SEQ ID NO 140
<211> LENGTH: 9
<212> TYPE: PRT
<213> ORGANISM: Artificial sequence
<220> FEATURE:
```

```
<223> OTHER INFORMATION: homologues of SEQ ID NO:1

<400> SEQUENCE: 140

Ile Val Ala Arg Pro Pro His Ile Gly
1               5

<210> SEQ ID NO 141
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 141

Ile Val Ala Arg Pro Pro Thr His Gly
1               5

<210> SEQ ID NO 142
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 142

Ile Val Ala Arg Pro Pro Thr Ile His
1               5

<210> SEQ ID NO 143
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 143

Cys Val Ala Arg Pro Pro Thr Ile Gly
1               5

<210> SEQ ID NO 144
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 144

Ile Cys Ala Arg Pro Pro Thr Ile Gly
1               5

<210> SEQ ID NO 145
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 145

Ile Val Cys Arg Pro Pro Thr Ile Gly
1               5

<210> SEQ ID NO 146
<211> LENGTH: 9
<212> TYPE: PRT
<213> ORGANISM: Artificial sequence
<220> FEATURE:
<223> OTHER INFORMATION: homologues of SEQ ID NO:1
```

```
<400> SEQUENCE: 146

Ile Val Ala Cys Pro Pro Thr Ile Gly
1               5

<210> SEQ ID NO 147
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 147

Ile Val Ala Arg Cys Pro Thr Ile Gly
1               5

<210> SEQ ID NO 148
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 148

Ile Val Ala Arg Pro Cys Thr Ile Gly
1               5

<210> SEQ ID NO 149
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 149

Ile Val Ala Arg Pro Pro Cys Ile Gly
1               5

<210> SEQ ID NO 150
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 150

Ile Val Ala Arg Pro Pro Thr Cys Gly
1               5

<210> SEQ ID NO 151
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 151

Ile Val Ala Arg Pro Pro Thr Ile Cys
1               5

<210> SEQ ID NO 152
<211> LENGTH: 9
<212> TYPE: PRT
<213> ORGANISM: Artificial sequence
<220> FEATURE:
<223> OTHER INFORMATION: homologues of SEQ ID NO:1
```

```
<400> SEQUENCE: 152

Asn Val Ala Arg Pro Pro Thr Ile Gly
1               5

<210> SEQ ID NO 153
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 153

Ile Asn Ala Arg Pro Pro Thr Ile Gly
1               5

<210> SEQ ID NO 154
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 154

Ile Val Asn Arg Pro Pro Thr Ile Gly
1               5

<210> SEQ ID NO 155
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 155

Ile Val Ala Asn Pro Pro Thr Ile Gly
1               5

<210> SEQ ID NO 156
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 156

Ile Val Ala Arg Asn Pro Thr Ile Gly
1               5

<210> SEQ ID NO 157
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 157

Ile Val Ala Arg Pro Asn Thr Ile Gly
1               5

<210> SEQ ID NO 158
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 158
```

```
Ile Val Ala Arg Pro Pro Asn Ile Gly
1               5

<210> SEQ ID NO 159
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 159

Ile Val Ala Arg Pro Pro Thr Asn Gly
1               5

<210> SEQ ID NO 160
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 160

Ile Val Ala Arg Pro Pro Thr Ile Asn
1               5

<210> SEQ ID NO 161
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 161

Gln Val Ala Arg Pro Pro Thr Ile Gly
1               5

<210> SEQ ID NO 162
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 162

Ile Gln Ala Arg Pro Pro Thr Ile Gly
1               5

<210> SEQ ID NO 163
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 163

Ile Val Gln Arg Pro Pro Thr Ile Gly
1               5

<210> SEQ ID NO 164
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 164
```

Ile Val Ala Gln Pro Pro Thr Ile Gly
1               5

<210> SEQ ID NO 165
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 165

Ile Val Ala Arg Gln Pro Thr Ile Gly
1               5

<210> SEQ ID NO 166
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 166

Ile Val Ala Arg Pro Gln Thr Ile Gly
1               5

<210> SEQ ID NO 167
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 167

Ile Val Ala Arg Pro Pro Gln Ile Gly
1               5

<210> SEQ ID NO 168
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 168

Ile Val Ala Arg Pro Pro Thr Gln Gly
1               5

<210> SEQ ID NO 169
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 169

Ile Val Ala Arg Pro Pro Thr Ile Gln
1               5

<210> SEQ ID NO 170
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 170

Trp Val Ala Arg Pro Pro Thr Ile Gly

```
1               5

<210> SEQ ID NO 171
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 171

Ile Trp Ala Arg Pro Pro Thr Ile Gly
1               5

<210> SEQ ID NO 172
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 172

Ile Val Trp Arg Pro Pro Thr Ile Gly
1               5

<210> SEQ ID NO 173
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 173

Ile Val Ala Trp Pro Pro Thr Ile Gly
1               5

<210> SEQ ID NO 174
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 174

Ile Val Ala Arg Trp Pro Thr Ile Gly
1               5

<210> SEQ ID NO 175
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 175

Ile Val Ala Arg Pro Trp Thr Ile Gly
1               5

<210> SEQ ID NO 176
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 176

Ile Val Ala Arg Pro Pro Trp Ile Gly
1               5
```

```
<210> SEQ ID NO 177
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 177

Ile Val Ala Arg Pro Pro Thr Trp Gly
1               5

<210> SEQ ID NO 178
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 178

Ile Val Ala Arg Pro Pro Thr Ile Trp
1               5

<210> SEQ ID NO 179
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 179

Ile Val Tyr Gln Val Pro Thr Ile Gly
1               5

<210> SEQ ID NO 180
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 180

Ile Val Ile Ser Val Pro Thr Ile Gly
1               5

<210> SEQ ID NO 181
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 181

Ile Val Thr Arg Val Pro Val Ile Gly
1               5

<210> SEQ ID NO 182
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 182

Ile Val Val Arg Asn Pro Thr Ala Gly
1               5
```

```
<210> SEQ ID NO 183
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 183

Thr Val Ala Lys Thr Pro Thr Ile Gly
1               5

<210> SEQ ID NO 184
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 184

Leu Val Val Ser Pro Pro Arg Ile Gly
1               5

<210> SEQ ID NO 185
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 185

Ile Val Ser Met Val Pro Lys Ile Gly
1               5

<210> SEQ ID NO 186
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 186

Lys Val Ile Arg Val Pro Arg Ile Gly
1               5

<210> SEQ ID NO 187
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 187

Ile Val Ile Arg Thr Pro Ile Ile Thr
1               5

<210> SEQ ID NO 188
<211> LENGTH: 9
<212> TYPE: PRT
<213> ORGANISM: Artificial sequence
<220> FEATURE:
<223> OTHER INFORMATION: homologues of SEQ ID NO:1

<400> SEQUENCE: 188

Val Val Thr Ser Val Pro His Ile Thr
1               5
```

```
<210> SEQ ID NO 189
<211> LENGTH: 9
<212> TYPE: PRT
<213> ORGANISM: Artificial sequence
<220> FEATURE:
<223> OTHER INFORMATION: homologues of SEQ ID NO:1
<220> FEATURE:
<221> NAME/KEY: misc_feature
<222> LOCATION: (6)
<223> OTHER INFORMATION: Xaa = cysteine or tryptophan
<220> FEATURE:
<221> NAME/KEY: misc_feature
<222> LOCATION: (7)
<223> OTHER INFORMATION: Xaa = phenylalanine or tryptophan

<400> SEQUENCE: 189

Arg Tyr Lys Tyr Gln Xaa Xaa Tyr Ile
1               5

<210> SEQ ID NO 190
<211> LENGTH: 9
<212> TYPE: PRT
<213> ORGANISM: Artificial sequence
<220> FEATURE:
<223> OTHER INFORMATION: optimal docking polypeptide of insulin receptor

<400> SEQUENCE: 190

Arg Tyr Lys Tyr Gln Trp Phe Tyr Ile
1               5

<210> SEQ ID NO 191
<211> LENGTH: 9
<212> TYPE: PRT
<213> ORGANISM: Artificial sequence
<220> FEATURE:
<223> OTHER INFORMATION: optimal docking polypeptide of insulin receptor

<400> SEQUENCE: 191

Arg Tyr Lys Tyr Gln Cys Phe Tyr Ile
1               5

<210> SEQ ID NO 192
<211> LENGTH: 9
<212> TYPE: PRT
<213> ORGANISM: Artificial sequence
<220> FEATURE:
<223> OTHER INFORMATION: optimal docking polypeptide of insulin receptor

<400> SEQUENCE: 192

Arg Tyr Lys Tyr Gln Trp Trp Tyr Ile
1               5

<210> SEQ ID NO 193
<211> LENGTH: 9
<212> TYPE: PRT
<213> ORGANISM: Artificial sequence
<220> FEATURE:
<223> OTHER INFORMATION: optimal docking polypeptide of insulin receptor

<400> SEQUENCE: 193

Arg Tyr Lys Tyr Gln Cys Trp Tyr Ile
1               5

<210> SEQ ID NO 194
<211> LENGTH: 9
<212> TYPE: PRT
<213> ORGANISM: Artificial sequence
<220> FEATURE:
<223> OTHER INFORMATION: homologues of SEQ ID NO:191
```

<400> SEQUENCE: 194

Arg Arg Lys Tyr Gln Cys Phe Tyr Ile
1               5

<210> SEQ ID NO 195
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 195

Arg Tyr Arg Tyr Gln Cys Phe Tyr Ile
1               5

<210> SEQ ID NO 196
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 196

Arg Tyr Lys Arg Gln Cys Phe Tyr Ile
1               5

<210> SEQ ID NO 197
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 197

Arg Tyr Lys Tyr Arg Cys Phe Tyr Ile
1               5

<210> SEQ ID NO 198
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 198

Arg Tyr Lys Tyr Gln Arg Phe Tyr Ile
1               5

<210> SEQ ID NO 199
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 199

Arg Tyr Lys Tyr Gln Cys Arg Tyr Ile
1               5

<210> SEQ ID NO 200
<211> LENGTH: 9
<212> TYPE: PRT
<213> ORGANISM: Artificial sequence
<220> FEATURE:
<223> OTHER INFORMATION: homologues of SEQ ID NO:191

```
<400> SEQUENCE: 200

Arg Tyr Lys Tyr Gln Cys Phe Arg Ile
1               5

<210> SEQ ID NO 201
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 201

Arg Tyr Lys Tyr Gln Cys Phe Tyr Arg
1               5

<210> SEQ ID NO 202
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 202

Ala Tyr Lys Tyr Gln Cys Phe Tyr Ile
1               5

<210> SEQ ID NO 203
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 203

Arg Ala Lys Tyr Gln Cys Phe Tyr Ile
1               5

<210> SEQ ID NO 204
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 204

Arg Tyr Ala Tyr Gln Cys Phe Tyr Ile
1               5

<210> SEQ ID NO 205
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 205

Arg Tyr Lys Ala Gln Cys Phe Tyr Ile
1               5

<210> SEQ ID NO 206
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 206
```

```
Arg Tyr Lys Tyr Ala Cys Phe Tyr Ile
1               5
```

<210> SEQ ID NO 207
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 207

```
Arg Tyr Lys Tyr Gln Ala Phe Tyr Ile
1               5
```

<210> SEQ ID NO 208
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 208

```
Arg Tyr Lys Tyr Gln Cys Ala Tyr Ile
1               5
```

<210> SEQ ID NO 209
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 209

```
Arg Tyr Lys Tyr Gln Cys Phe Ala Ile
1               5
```

<210> SEQ ID NO 210
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 210

```
Arg Tyr Lys Tyr Gln Cys Phe Tyr Ala
1               5
```

<210> SEQ ID NO 211
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 211

```
Val Tyr Lys Tyr Gln Cys Phe Tyr Ile
1               5
```

<210> SEQ ID NO 212
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 212

Arg Val Lys Tyr Gln Cys Phe Tyr Ile
1               5

<210> SEQ ID NO 213
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 213

Arg Tyr Val Tyr Gln Cys Phe Tyr Ile
1               5

<210> SEQ ID NO 214
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 214

Arg Tyr Lys Val Gln Cys Phe Tyr Ile
1               5

<210> SEQ ID NO 215
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 215

Arg Tyr Lys Tyr Val Cys Phe Tyr Ile
1               5

<210> SEQ ID NO 216
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 216

Arg Tyr Lys Tyr Gln Val Phe Tyr Ile
1               5

<210> SEQ ID NO 217
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 217

Arg Tyr Lys Tyr Gln Cys Val Tyr Ile
1               5

<210> SEQ ID NO 218
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 218

Arg Tyr Lys Tyr Gln Cys Phe Val Ile

<210> SEQ ID NO 219
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 219

Arg Tyr Lys Tyr Gln Cys Phe Tyr Val
1               5

<210> SEQ ID NO 220
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 220

Phe Tyr Lys Tyr Gln Cys Phe Tyr Ile
1               5

<210> SEQ ID NO 221
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 221

Arg Phe Lys Tyr Gln Cys Phe Tyr Ile
1               5

<210> SEQ ID NO 222
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 222

Arg Tyr Phe Tyr Gln Cys Phe Tyr Ile
1               5

<210> SEQ ID NO 223
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 223

Arg Tyr Lys Phe Gln Cys Phe Tyr Ile
1               5

<210> SEQ ID NO 224
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 224

Arg Tyr Lys Tyr Phe Cys Phe Tyr Ile
1               5

```
<210> SEQ ID NO 225
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 225

Arg Tyr Lys Tyr Gln Phe Phe Tyr Ile
1               5

<210> SEQ ID NO 226
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 226

Arg Tyr Lys Tyr Gln Cys Phe Phe Ile
1               5

<210> SEQ ID NO 227
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 227

Arg Tyr Lys Tyr Gln Cys Phe Tyr Phe
1               5

<210> SEQ ID NO 228
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 228

Pro Tyr Lys Tyr Gln Cys Phe Tyr Ile
1               5

<210> SEQ ID NO 229
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 229

Arg Pro Lys Tyr Gln Cys Phe Tyr Ile
1               5

<210> SEQ ID NO 230
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 230

Arg Tyr Pro Tyr Gln Cys Phe Tyr Ile
1               5
```

```
<210> SEQ ID NO 231
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 231

Arg Tyr Lys Pro Gln Cys Phe Tyr Ile
1               5

<210> SEQ ID NO 232
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 232

Arg Tyr Lys Tyr Pro Cys Phe Tyr Ile
1               5

<210> SEQ ID NO 233
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 233

Arg Tyr Lys Tyr Gln Pro Phe Tyr Ile
1               5

<210> SEQ ID NO 234
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 234

Arg Tyr Lys Tyr Gln Cys Pro Tyr Ile
1               5

<210> SEQ ID NO 235
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 235

Arg Tyr Lys Tyr Gln Cys Phe Pro Ile
1               5

<210> SEQ ID NO 236
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 236

Arg Tyr Lys Tyr Gln Cys Phe Tyr Pro
1               5
```

<210> SEQ ID NO 237
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 237

Met Tyr Lys Tyr Gln Cys Phe Tyr Ile
1               5

<210> SEQ ID NO 238
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 238

Arg Met Lys Tyr Gln Cys Phe Tyr Ile
1               5

<210> SEQ ID NO 239
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 239

Arg Tyr Met Tyr Gln Cys Phe Tyr Ile
1               5

<210> SEQ ID NO 240
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 240

Arg Tyr Lys Met Gln Cys Phe Tyr Ile
1               5

<210> SEQ ID NO 241
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 241

Arg Tyr Lys Tyr Met Cys Phe Tyr Ile
1               5

<210> SEQ ID NO 242
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 242

Arg Tyr Lys Tyr Gln Met Phe Tyr Ile
1               5

<210> SEQ ID NO 243

```
<210> SEQ ID NO 243
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 243

Arg Tyr Lys Tyr Gln Cys Met Tyr Ile
1               5

<210> SEQ ID NO 244
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 244

Arg Tyr Lys Tyr Gln Cys Phe Met Ile
1               5

<210> SEQ ID NO 245
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 245

Arg Tyr Lys Tyr Gln Cys Phe Tyr Met
1               5

<210> SEQ ID NO 246
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 246

Ile Tyr Lys Tyr Gln Cys Phe Tyr Ile
1               5

<210> SEQ ID NO 247
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 247

Arg Ile Lys Tyr Gln Cys Phe Tyr Ile
1               5

<210> SEQ ID NO 248
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 248

Arg Tyr Ile Tyr Gln Cys Phe Tyr Ile
1               5

<210> SEQ ID NO 249
<211> LENGTH: 9
```

```
<212> TYPE: PRT
<213> ORGANISM: Artificial sequence
<220> FEATURE:
<223> OTHER INFORMATION: homologues of SEQ ID NO:191

<400> SEQUENCE: 249

Arg Tyr Lys Ile Gln Cys Phe Tyr Ile
1               5

<210> SEQ ID NO 250
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 250

Arg Tyr Lys Tyr Ile Cys Phe Tyr Ile
1               5

<210> SEQ ID NO 251
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 251

Arg Tyr Lys Tyr Gln Ile Phe Tyr Ile
1               5

<210> SEQ ID NO 252
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 252

Arg Tyr Lys Tyr Gln Cys Ile Tyr Ile
1               5

<210> SEQ ID NO 253
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 253

Arg Tyr Lys Tyr Gln Cys Phe Ile Ile
1               5

<210> SEQ ID NO 254
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 254

Leu Tyr Lys Tyr Gln Cys Phe Tyr Ile
1               5

<210> SEQ ID NO 255
<211> LENGTH: 9
<212> TYPE: PRT
```

```
<213> ORGANISM: Artificial sequence
<220> FEATURE:
<223> OTHER INFORMATION: homologues of SEQ ID NO:191

<400> SEQUENCE: 255

Arg Leu Lys Tyr Gln Cys Phe Tyr Ile
1               5

<210> SEQ ID NO 256
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 256

Arg Tyr Leu Tyr Gln Cys Phe Tyr Ile
1               5

<210> SEQ ID NO 257
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 257

Arg Tyr Lys Leu Gln Cys Phe Tyr Ile
1               5

<210> SEQ ID NO 258
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 258

Arg Tyr Lys Tyr Leu Cys Phe Tyr Ile
1               5

<210> SEQ ID NO 259
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 259

Arg Tyr Lys Tyr Gln Leu Phe Tyr Ile
1               5

<210> SEQ ID NO 260
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 260

Arg Tyr Lys Tyr Gln Cys Leu Tyr Ile
1               5

<210> SEQ ID NO 261
<211> LENGTH: 9
<212> TYPE: PRT
<213> ORGANISM: Artificial sequence
```

```
<220> FEATURE:
<223> OTHER INFORMATION: homologues of SEQ ID NO:191

<400> SEQUENCE: 261

Arg Tyr Lys Tyr Gln Cys Phe Leu Ile
1               5

<210> SEQ ID NO 262
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 262

Arg Tyr Lys Tyr Gln Cys Phe Tyr Leu
1               5

<210> SEQ ID NO 263
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 263

Asp Tyr Lys Tyr Gln Cys Phe Tyr Ile
1               5

<210> SEQ ID NO 264
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 264

Arg Asp Lys Tyr Gln Cys Phe Tyr Ile
1               5

<210> SEQ ID NO 265
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 265

Arg Tyr Asp Tyr Gln Cys Phe Tyr Ile
1               5

<210> SEQ ID NO 266
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 266

Arg Tyr Lys Asp Gln Cys Phe Tyr Ile
1               5

<210> SEQ ID NO 267
<211> LENGTH: 9
<212> TYPE: PRT
<213> ORGANISM: Artificial sequence
<220> FEATURE:
```

<223> OTHER INFORMATION: homologues of SEQ ID NO:191

<400> SEQUENCE: 267

Arg Tyr Lys Tyr Asp Cys Phe Tyr Ile
1               5

<210> SEQ ID NO 268
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 268

Arg Tyr Lys Tyr Gln Asp Phe Tyr Ile
1               5

<210> SEQ ID NO 269
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 269

Arg Tyr Lys Tyr Gln Cys Asp Tyr Ile
1               5

<210> SEQ ID NO 270
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 270

Arg Tyr Lys Tyr Gln Cys Phe Asp Ile
1               5

<210> SEQ ID NO 271
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 271

Arg Tyr Lys Tyr Gln Cys Phe Tyr Asp
1               5

<210> SEQ ID NO 272
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 272

Glu Tyr Lys Tyr Gln Cys Phe Tyr Ile
1               5

<210> SEQ ID NO 273
<211> LENGTH: 9
<212> TYPE: PRT
<213> ORGANISM: Artificial sequence
<220> FEATURE:
<223> OTHER INFORMATION: homologues of SEQ ID NO:191

```
<400> SEQUENCE: 273

Arg Glu Lys Tyr Gln Cys Phe Tyr Ile
1               5

<210> SEQ ID NO 274
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 274

Arg Tyr Glu Tyr Gln Cys Phe Tyr Ile
1               5

<210> SEQ ID NO 275
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 275

Arg Tyr Lys Glu Gln Cys Phe Tyr Ile
1               5

<210> SEQ ID NO 276
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 276

Arg Tyr Lys Tyr Glu Cys Phe Tyr Ile
1               5

<210> SEQ ID NO 277
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 277

Arg Tyr Lys Tyr Gln Glu Phe Tyr Ile
1               5

<210> SEQ ID NO 278
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 278

Arg Tyr Lys Tyr Gln Cys Glu Tyr Ile
1               5

<210> SEQ ID NO 279
<211> LENGTH: 9
<212> TYPE: PRT
<213> ORGANISM: Artificial sequence
<220> FEATURE:
<223> OTHER INFORMATION: homologues of SEQ ID NO:191
```

```
<400> SEQUENCE: 279

Arg Tyr Lys Tyr Gln Cys Phe Glu Ile
1               5

<210> SEQ ID NO 280
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 280

Arg Tyr Lys Tyr Gln Cys Phe Tyr Glu
1               5

<210> SEQ ID NO 281
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 281

Lys Tyr Lys Tyr Gln Cys Phe Tyr Ile
1               5

<210> SEQ ID NO 282
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 282

Arg Lys Lys Tyr Gln Cys Phe Tyr Ile
1               5

<210> SEQ ID NO 283
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 283

Arg Tyr Lys Lys Gln Cys Phe Tyr Ile
1               5

<210> SEQ ID NO 284
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 284

Arg Tyr Lys Tyr Lys Cys Phe Tyr Ile
1               5

<210> SEQ ID NO 285
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 285
```

```
Arg Tyr Lys Tyr Gln Lys Phe Tyr Ile
1               5
```

<210> SEQ ID NO 286
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 286

```
Arg Tyr Lys Tyr Gln Cys Lys Tyr Ile
1               5
```

<210> SEQ ID NO 287
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 287

```
Arg Tyr Lys Tyr Gln Cys Phe Lys Ile
1               5
```

<210> SEQ ID NO 288
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 288

```
Arg Tyr Lys Tyr Gln Cys Phe Tyr Lys
1               5
```

<210> SEQ ID NO 289
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 289

```
Gly Tyr Lys Tyr Gln Cys Phe Tyr Ile
1               5
```

<210> SEQ ID NO 290
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 290

```
Arg Gly Lys Tyr Gln Cys Phe Tyr Ile
1               5
```

<210> SEQ ID NO 291
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 291

```
Arg Tyr Gly Tyr Gln Cys Phe Tyr Ile
1               5
```

<210> SEQ ID NO 292
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 292

```
Arg Tyr Lys Gly Gln Cys Phe Tyr Ile
1               5
```

<210> SEQ ID NO 293
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 293

```
Arg Tyr Lys Tyr Gly Cys Phe Tyr Ile
1               5
```

<210> SEQ ID NO 294
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 294

```
Arg Tyr Lys Tyr Gln Gly Phe Tyr Ile
1               5
```

<210> SEQ ID NO 295
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 295

```
Arg Tyr Lys Tyr Gln Cys Gly Tyr Ile
1               5
```

<210> SEQ ID NO 296
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 296

```
Arg Tyr Lys Tyr Gln Cys Phe Gly Ile
1               5
```

<210> SEQ ID NO 297
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 297

```
Arg Tyr Lys Tyr Gln Cys Phe Tyr Gly
```

```
1               5

<210> SEQ ID NO 298
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 298

Ser Tyr Lys Tyr Gln Cys Phe Tyr Ile
1               5

<210> SEQ ID NO 299
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 299

Arg Ser Lys Tyr Gln Cys Phe Tyr Ile
1               5

<210> SEQ ID NO 300
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 300

Arg Tyr Ser Tyr Gln Cys Phe Tyr Ile
1               5

<210> SEQ ID NO 301
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 301

Arg Tyr Lys Ser Gln Cys Phe Tyr Ile
1               5

<210> SEQ ID NO 302
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 302

Arg Tyr Lys Tyr Ser Cys Phe Tyr Ile
1               5

<210> SEQ ID NO 303
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 303

Arg Tyr Lys Tyr Gln Ser Phe Tyr Ile
1               5
```

```
<210> SEQ ID NO 304
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 304

Arg Tyr Lys Tyr Gln Cys Ser Tyr Ile
1               5

<210> SEQ ID NO 305
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 305

Arg Tyr Lys Tyr Gln Cys Phe Ser Ile
1               5

<210> SEQ ID NO 306
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 306

Arg Tyr Lys Tyr Gln Cys Phe Tyr Ser
1               5

<210> SEQ ID NO 307
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 307

Thr Tyr Lys Tyr Gln Cys Phe Tyr Ile
1               5

<210> SEQ ID NO 308
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 308

Arg Thr Lys Tyr Gln Cys Phe Tyr Ile
1               5

<210> SEQ ID NO 309
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 309

Arg Tyr Thr Tyr Gln Cys Phe Tyr Ile
1               5
```

<210> SEQ ID NO 310
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 310

Arg Tyr Lys Thr Gln Cys Phe Tyr Ile
1               5

<210> SEQ ID NO 311
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 311

Arg Tyr Lys Tyr Thr Cys Phe Tyr Ile
1               5

<210> SEQ ID NO 312
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 312

Arg Tyr Lys Tyr Gln Thr Phe Tyr Ile
1               5

<210> SEQ ID NO 313
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 313

Arg Tyr Lys Tyr Gln Cys Thr Tyr Ile
1               5

<210> SEQ ID NO 314
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 314

Arg Tyr Lys Tyr Gln Cys Phe Thr Ile
1               5

<210> SEQ ID NO 315
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 315

Arg Tyr Lys Tyr Gln Cys Phe Tyr Thr
1               5

```
<210> SEQ ID NO 316
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 316

Tyr Tyr Lys Tyr Gln Cys Phe Tyr Ile
1               5

<210> SEQ ID NO 317
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 317

Arg Tyr Tyr Tyr Gln Cys Phe Tyr Ile
1               5

<210> SEQ ID NO 318
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 318

Arg Tyr Lys Tyr Tyr Cys Phe Tyr Ile
1               5

<210> SEQ ID NO 319
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 319

Arg Tyr Lys Tyr Gln Tyr Phe Tyr Ile
1               5

<210> SEQ ID NO 320
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 320

Arg Tyr Lys Tyr Gln Cys Tyr Tyr Ile
1               5

<210> SEQ ID NO 321
<211> LENGTH: 9
<212> TYPE: PRT
<213> ORGANISM: Artificial sequence
<220> FEATURE:
<223> OTHER INFORMATION: homologues of SEQ ID NO:191
```

```
<400> SEQUENCE: 321

Arg Tyr Lys Tyr Gln Cys Phe Tyr Tyr
1               5

<210> SEQ ID NO 322
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 322

His Tyr Lys Tyr Gln Cys Phe Tyr Ile
1               5

<210> SEQ ID NO 323
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 323

Arg His Lys Tyr Gln Cys Phe Tyr Ile
1               5

<210> SEQ ID NO 324
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 324

Arg Tyr His Tyr Gln Cys Phe Tyr Ile
1               5

<210> SEQ ID NO 325
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 325

Arg Tyr Lys His Gln Cys Phe Tyr Ile
1               5

<210> SEQ ID NO 326
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 326

Arg Tyr Lys Tyr His Cys Phe Tyr Ile
1               5

<210> SEQ ID NO 327
<211> LENGTH: 9
<212> TYPE: PRT
<213> ORGANISM: Artificial sequence
<220> FEATURE:
<223> OTHER INFORMATION: homologues of SEQ ID NO:191
```

```
<400> SEQUENCE: 327

Arg Tyr Lys Tyr Gln His Phe Tyr Ile
1               5

<210> SEQ ID NO 328
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 328

Arg Tyr Lys Tyr Gln Cys His Tyr Ile
1               5

<210> SEQ ID NO 329
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 329

Arg Tyr Lys Tyr Gln Cys Phe His Ile
1               5

<210> SEQ ID NO 330
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 330

Arg Tyr Lys Tyr Gln Cys Phe Tyr His
1               5

<210> SEQ ID NO 331
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 331

Cys Tyr Lys Tyr Gln Cys Phe Tyr Ile
1               5

<210> SEQ ID NO 332
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 332

Arg Cys Lys Tyr Gln Cys Phe Tyr Ile
1               5

<210> SEQ ID NO 333
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 333
```

Arg Tyr Cys Tyr Gln Cys Phe Tyr Ile
1               5

<210> SEQ ID NO 334
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 334

Arg Tyr Lys Cys Gln Cys Phe Tyr Ile
1               5

<210> SEQ ID NO 335
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 335

Arg Tyr Lys Tyr Cys Cys Phe Tyr Ile
1               5

<210> SEQ ID NO 336
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 336

Arg Tyr Lys Tyr Gln Cys Cys Tyr Ile
1               5

<210> SEQ ID NO 337
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 337

Arg Tyr Lys Tyr Gln Cys Phe Cys Ile
1               5

<210> SEQ ID NO 338
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 338

Arg Tyr Lys Tyr Gln Cys Phe Tyr Cys
1               5

<210> SEQ ID NO 339
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 339

Asn Tyr Lys Tyr Gln Cys Phe Tyr Ile
1               5

<210> SEQ ID NO 340
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 340

Arg Asn Lys Tyr Gln Cys Phe Tyr Ile
1               5

<210> SEQ ID NO 341
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 341

Arg Tyr Asn Tyr Gln Cys Phe Tyr Ile
1               5

<210> SEQ ID NO 342
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 342

Arg Tyr Lys Asn Gln Cys Phe Tyr Ile
1               5

<210> SEQ ID NO 343
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 343

Arg Tyr Lys Tyr Asn Cys Phe Tyr Ile
1               5

<210> SEQ ID NO 344
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 344

Arg Tyr Lys Tyr Gln Asn Phe Tyr Ile
1               5

<210> SEQ ID NO 345
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 345

Arg Tyr Lys Tyr Gln Cys Asn Tyr Ile

```
1               5
```

<210> SEQ ID NO 346
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 346

```
Arg Tyr Lys Tyr Gln Cys Phe Asn Ile
1               5
```

<210> SEQ ID NO 347
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 347

```
Arg Tyr Lys Tyr Gln Cys Phe Tyr Asn
1               5
```

<210> SEQ ID NO 348
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 348

```
Gln Tyr Lys Tyr Gln Cys Phe Tyr Ile
1               5
```

<210> SEQ ID NO 349
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 349

```
Arg Gln Lys Tyr Gln Cys Phe Tyr Ile
1               5
```

<210> SEQ ID NO 350
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 350

```
Arg Tyr Gln Tyr Gln Cys Phe Tyr Ile
1               5
```

<210> SEQ ID NO 351
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 351

```
Arg Tyr Lys Gln Gln Cys Phe Tyr Ile
1               5
```

```
<210> SEQ ID NO 352
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 352

Arg Tyr Lys Tyr Gln Gln Phe Tyr Ile
1               5

<210> SEQ ID NO 353
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 353

Arg Tyr Lys Tyr Gln Cys Gln Tyr Ile
1               5

<210> SEQ ID NO 354
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 354

Arg Tyr Lys Tyr Gln Cys Phe Gln Ile
1               5

<210> SEQ ID NO 355
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 355

Arg Tyr Lys Tyr Gln Cys Phe Tyr Gln
1               5

<210> SEQ ID NO 356
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 356

Trp Tyr Lys Tyr Gln Cys Phe Tyr Ile
1               5

<210> SEQ ID NO 357
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 357

Arg Trp Lys Tyr Gln Cys Phe Tyr Ile
1               5
```

<210> SEQ ID NO 358
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 358

Arg Tyr Trp Tyr Gln Cys Phe Tyr Ile
1               5

<210> SEQ ID NO 359
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 359

Arg Tyr Lys Trp Gln Cys Phe Tyr Ile
1               5

<210> SEQ ID NO 360
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 360

Arg Tyr Lys Tyr Trp Cys Phe Tyr Ile
1               5

<210> SEQ ID NO 361
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 361

Arg Tyr Lys Tyr Gln Trp Phe Tyr Ile
1               5

<210> SEQ ID NO 362
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 362

Arg Tyr Lys Tyr Gln Cys Trp Tyr Ile
1               5

<210> SEQ ID NO 363
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 363

Arg Tyr Lys Tyr Gln Cys Phe Trp Ile
1               5

```
<210> SEQ ID NO 364
<211> LENGTH: 9
<212> TYPE: PRT
<213> ORGANISM: Artificial sequence
<220> FEATURE:
<223> OTHER INFORMATION: homologues of SEQ ID NO:191

<400> SEQUENCE: 364

Arg Tyr Lys Tyr Gln Cys Phe Tyr Trp
1               5
```

US 9,029,326 B2

POLYPEPTIDES, NUCLEIC ACID MOLECULE ENCODING POLYPEPTIDES, AND USES OF POLYPEPTIDES

CLAIM FOR PRIORITY

This application is a Divisional application of U.S. patent application Ser. No. 13/557,374, entitled "Polypeptides, Nucleic Acid Molecule Encoding Polypeptides, And Uses Of Polypeptides", filed Jul. 25, 2012, currently allowed. U.S. patent application Ser. No. 13/557,374 is based upon Taiwan Patent Application No. 101117779, filed on May 18, 2012 in the Taiwan Intellectual Property Office. The priorities of U.S. patent application Ser. No. 13/557,374 and Taiwan Patent Application No. 101117779 are hereby claimed and the disclosure of both applications is incorporated herein in their entireties by reference.

CROSS-REFERENCES TO RELATED APPLICATIONS

Not applicable.

BACKGROUND OF THE INVENTION

1. Field of the Invention

The present invention relates to a polypeptide and use of the same, especially to a polypeptide which can bind to insulin receptors and is effective in reducing blood sugar, reducing glycated hemoglobin, and ameliorating hepato-renal disorders caused by diabetes.

2. Descriptions of the Related Art

Diabetes is a chronic illness of metabolic abnormality. The main cause of diabetes is a lack of insulin, a defective function of insulin in the body, or the resistance to insulin caused by the combination of innate gene defects and the postnatal environment. As a result, there is a low ability of using sugar, or even leading to the complete loss of the ability, thus, further elevating blood sugar and negatively affecting the metabolism of proteins and lipids in the body. In addition, diabetes brings other chronic complications, including the pathological changes of the ocular fundus, nerve (including motor nerve, sensory nerve, and autonomic nerve), liver and kidney, great vessels (including cerebrovascular obstruction, coronary artery disease, the occlusion of peripheral vessels), diabetes foot, etc.

According to the statistics from the World Health Organization (WHO), the number of diabetic patients around the world has increased dramatically, from about 30 million in 1985 to more than 171 million in 2000. The WHO further indicates that the number of worldwide diabetes patients will be more than 346 million in 2030. Moreover, the medical cost for diabetes and its complications in the U.S. increased from 44 billion USD in 1997 to 174 billion USD in 2007. With the increased prevalence of diabetes, it is important to develop a substance or medication that can efficiently modulate blood sugar.

Since 1922, insulin has been mainly used for treating diabetes. However, the lack of insulin is only part of the cause for the abnormality of pancreas function. Hence, using solely insulin to treat diabetes has limited efficiency.

Besides insulin, there are other pharmaceutical agents used to treat diabetes. These pharmaceutical agents, used for reducing blood sugar, can be classified into five groups according to their mechanisms. The first group consists of sulfonylureas (SU), which promote the secretion of insulin from the pancreas and increase the number of insulin receptors of histiocytes. The second group consists of benzoic acid derivatives, capable of stimulating the secretion of insulin. The third group consists of biguanides, which inhibit the absorption of sugar in the stomach or intestine, inhibit the production of sugar in the liver, and promote the intake of sugar in tissues. The fourth group consists of α-glucosidase inhibitors, which prevent disaccharides from being degraded into monosaccharides that can be absorbed by the intestines. The fifth group consists of insulin sensitizers, which alleviate the resistance of peripheral tissues and hepatocytes to insulin. Nevertheless, each group of the aforesaid pharmaceutical agents has different side effects. For example, sulfonylureas may cause rashes and a low level of blood sugar; benzoic acid derivatives may decrease the level of blood sugar; biguanides may cause lactic acidosis and stomach and intestine illnesses; α-glucosidase inhibitors may cause stomach and intestine illnesses; and insulin sensitizers may lead to the abnormality of liver function and injury to hepatocytes. Accordingly, it is important to develop a medication with a blood sugar-reducing function and fewer side effects.

Unlike common compounds, polypeptides better regulate metabolism and are better received by organisms, and thus, have fewer side effects. Therefore, many polypeptides have been studied in the world for decades and have been applied in clinical treatment. For instance, TW 1283684 discloses a Glucagon-Like Peptide-1 analogue, which reduces blood sugar, while U.S. Pat. No. 7,393,919 discloses medication for reducing blood sugar using Human proIslet Peptide (HIP), wherein the HIP is an active fragment of a pancreatitis-associated protein precursor.

Furthermore, polypeptides have been found to have blood sugar-reducing activity and can be obtained from plant extracts. For example, U.S. Pat. No. 6,127,338 discloses a polypeptide with blood sugar-reducing activity from bitter melon. The amino acid sequence of the polypeptide is KTNMKHMAGAAAAGAVVG, while the molecular weight of the polypeptide is less than 10 kDa.

Consequently, even though there are a lot of pharmaceutical agents for modulating blood sugar, a single or combined treating method or a pharmaceutical composition for treating diabetes with different morbific mechanisms is still needed.

The present invention researches the aforesaid requirement, and provides a novel polypeptide which can bind to insulin receptors and is effective in reducing blood sugar, reducing glycated hemoglobin, and ameliorating hepato-renal disorders caused by diabetes, especially, can be used to treat diabetes.

SUMMARY OF THE INVENTION

One objective of this invention is to provide a polypeptide having a segmental amino acid sequence of SEQ ID NO:1 selected from the group consisting of SEQ ID NO:2, SEQ ID NO:3, SEQ ID NO:4, SEQ ID NO:5, and SEQ ID NO:6.

Another objective of this invention is to provide a polypeptide having an amino acid sequence of IVARPPTIG (SEQ ID NO:7) or a homologous amino acid sequence derived from the substitution of a single amino acid in SEQ ID NO:7, wherein the homologous amino acid sequence is an amino acid sequence selected from the group consisting of SEQ ID NO:8 to SEQ ID NO:178.

Yet a further objective of this invention is to provide a polypeptide having an amino acid sequence selected from the group consisting of SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, and SEQ ID NO:188.

Yet a further objective of this invention is to provide a polypeptide having an amino acid sequence of RYKYQX$_1$X$_2$YI (SEQ ID NO: 189) or a homologous amino acid sequence derived from the substitution of a single amino acid in SEQ ID NO: 189, wherein X$_1$ is cysteine or tryptophan and X$_2$ is phenylalanine or tryptophan.

Yet a further objective of this invention is to provide an isolated nucleic acid molecule encoding the polypeptide as defined above.

Yet a further objective of this invention is to provide a pharmaceutical composition which can bind to insulin receptors (IR) and is effective in reducing blood sugar, reducing glycated hemoglobin, and ameliorating hepato-renal disorders caused by diabetes, comprising the polypeptide as defined above and a pharmaceutically acceptable carrier.

Yet a further objective of this invention is to provide a method for at least one of reducing blood sugar, reducing glycated hemoglobin, and ameliorating hepato-renal disorders caused by diabetes in a subject, comprising administrating to the subject an effective amount of the polypeptide as defined above.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
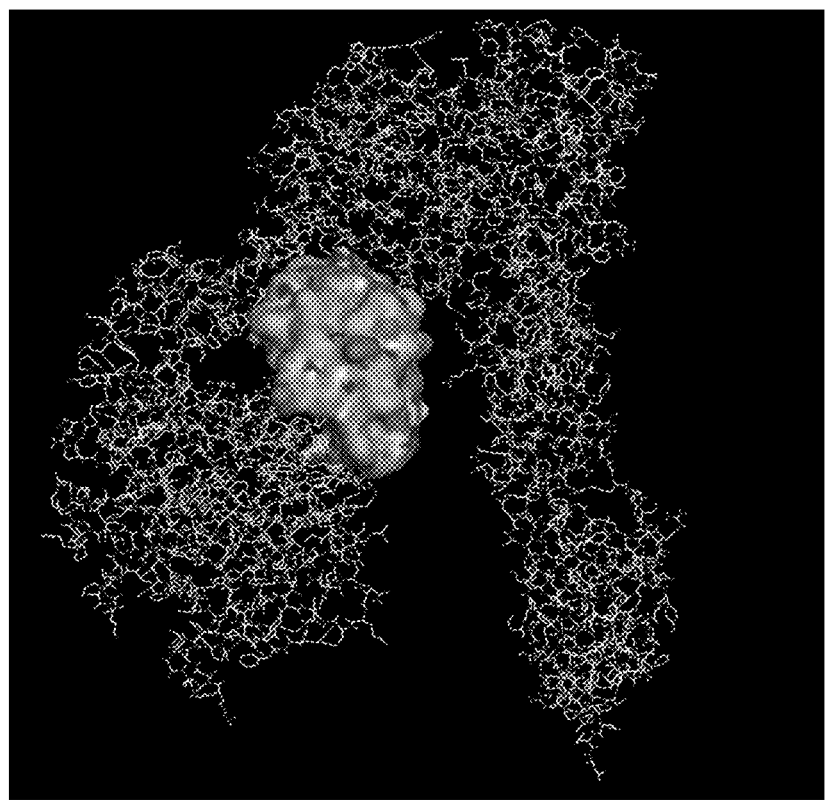
FIG. 1 is a molecular docking image showing IRBP-1-68 (SEQ ID NO:1) and an insulin receptor.

The following will describe some embodiments of the present invention in detail. However, without departing from the spirit of the present invention, the present invention may be embodied in various embodiments and should not be limited to the embodiments described in the specification. In addition, unless otherwise stated herein, the terms "a (an)", "the" or the like used in this specification (especially in the Claims hereinafter) shall be understood to encompass both the singular form and the plural form.

The term "homologous amino acid sequence" used in this specification, unless otherwise stated herein, refers to an amino acid sequence derived from the substitution of one or more amino acids in the amino acid sequence of a polypeptide. Furthermore, the term "homologous polypeptide" used in this specification, unless otherwise stated herein, refers to a polypeptide homologue derived from the substitution of one or more amino acids in the amino acid sequence of a polypeptide.

It has been known that when a ligand like insulin combines with an insulin receptor (IR) in a cell, it will result in the autophosphorylation of the insulin receptor, and thereby, trigger signal transduction reactions downstream, inducing the transcription and translation of related genes, and triggering glucose transportation to reduce the extracellular glucose concentration or the glucose concentration in blood and achieve the effect of reducing blood sugar.

The inventors of the present invention found that when dividing a polypeptide having an amino sequence of SEQ ID NO:1 (68 amino acids in total) into different segments, or further modify said segments by a single or multiple amino acids mutation technology, it can provide various polypeptides. Said polypeptides can bind with insulin receptors, and can reduce blood-sugar, reduce glycated hemoglobin, and ameliorate hepato-renal disorders caused by diabetes. Without being limited by the theory, it is believed that the polypeptide of the present invention can bind with an insulin receptor, thereby triggering the mechanism of the autophosphorylation of the insulin receptor and achieving the aforesaid effects.

Therefore, the present invention provides a first polypeptide, which is obtained by dividing a polypeptide having the amino acid sequence of SEQ ID NO:1 (68 amino acids in total) and has a segmental amino acid sequence of SEQ ID NO:1 selected from the group consisting of SEQ ID NO:2, SEQ ID NO:3, SEQ ID NO:4, SEQ ID NO:5, and SEQ ID NO:6. The amino acid sequence of the first polypeptide is preferred to be an amino acid sequence of SEQ ID NO:2 or SEQ ID NO:6. Herein, SEQ ID NO:2 is a segmental amino acid sequence representing an amino acid sequence consisting of the 1$^{st}$ to 19$^{th}$ amino acids in the amino acid sequence of SEQ ID NO:1; SEQ ID NO:3 is a segmental amino acid sequence representing an amino acid sequence consisting of the 17$^{th}$ to 35$^{th}$ amino acids in the amino acid sequence of SEQ ID NO:1; SEQ ID NO:4 is a segmental amino acid sequence representing an amino acid sequence consisting of the 34$^{th}$ to 52$^{nd}$ amino acids in the amino acid sequence of SEQ ID NO:1; SEQ ID NO:5 is a segmental amino acid sequence representing an amino acid sequence consisting of the 45$^{th}$ to 68$^{th}$ amino acids in the amino acid sequence of SEQ ID NO:1; SEQ ID NO:6 is a segmental amino acid sequence representing an amino acid sequence consisting of the 55$^{th}$ to 68$^{th}$ amino acids in the amino acid sequence of SEQ ID NO:1. Hereinafter, the polypeptide of the present invention will be referred to as "insulin receptor-binding protein; IRBP". For example, the polypeptide of the present invention having the amino acid sequence consisting of the 68 amino acids described in SEQ ID NO:1 is referred to as "IRBP-1-68", while the polypeptide having the amino acid of SEQ ID NO:2 (i.e., the segmental amino acid sequence representing an amino acid sequence consisting of the 1$^{st}$ to 19$^{th}$ amino acids in the amino acid sequence of SEQ ID NO:1) is referred to as "IRBP-1-19".

The present invention also provides a second polypeptide having the following amino acid sequence or a homologous amino acid sequence of SEQ ID NO:7:

IVARPPTIG (SEQ ID NO:7);

wherein the SEQ ID NO:7 is a segmental amino acid sequence representing an amino acid sequence consisting of the 60$^{th}$ to 68$^{th}$ amino acids in the amino acid sequence of SEQ ID NO:1 (i.e., IRBP-60-68), which is divided from the amino acid sequence of SEQ ID NO:1. The homologous amino acid sequence is obtained by performing a single amino acid substitution technology to the amino acids in the amino acid sequence of SEQ ID NO:7 by different amino acids, and representing an amino acid sequence selected from the group consisting of SEQ ID NO:8 to SEQ ID NO:178. The second polypeptide is preferred to be an amino acid sequence of SEQ ID NO:7 or SEQ ID NO:21.

Furthermore, the present invention also provides a third polypeptide, which is obtained by performing amino acid mutation/substitution to 3 to 6 amino acids in IRBP-60-68 (SEQ ID NO:7) by different amino acids (i.e., replacement of 3 to 6 amino acids), and has an amino acid sequence selected from the group consisting of SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, and SEQ ID NO:188. Preferably, the third polypeptide has an amino acid sequence selected from the group consisting of SEQ ID NO:179, SEQ ID NO:184, SEQ ID NO:185, and SEQ ID NO:186.

The present invention also provides a fourth polypeptide having the following amino acid sequence or a homologous amino acid sequence derived from the substitution of a single amino acid in the following amino acid sequence:

RYKYQX$_1$X$_2$YI (SEQ ID NO: 189);

wherein X$_1$ is cysteine or tryptophan and X$_2$ is phenylalanine or tryptophan. The fourth polypeptide of the present invention is obtained by performing amino acid substitution to 9 amino acids in IRBP-60-68 (SEQ ID NO:7), and also can bind with an insulin receptor to reduce blood sugar levels.

In one embodiment of the present invention, the fourth polypeptide has an amino acid sequence of SEQ ID NO: 189. X$_1$ is preferred to be cysteine, while X$_2$ is preferred to be phenylalanine or tryptophan. In another embodiment of the present invention, the fourth polypeptide has an amino acid sequence of RYKYQCFYI (SEQ ID NO: 191) (i.e., X$_1$ is cysteine and X$_2$ is phenylalanine), or has a homologous amino acid sequence derived from the mutation/substitution of a single amino acid in SEQ ID NO: 191, wherein the homologous amino acid sequence is an amino acid sequence selected from the group consisting of SEQ ID NO:194 to SEQ ID NO:364.

All of the first to fourth polypeptides of the present invention can bind with an insulin receptor and reduce blood sugar, and thus, can be used to treat diabetes (including type I diabetes and type II diabetes) and improve the sequential processing of patients with diabetes, such as reducing glycated hemoglobin and ameliorating hepato-renal disorders caused by diabetes.

As compared with the insulin used in clinical settings for treating diabetes and the IRBP-1-68 polypeptide (SEQ ID NO:1) disclosed in the patents of TW 1342781 and JP 4772884, the polypeptides of the present invention have the following advantages: first, the polypeptides of the present invention have a shorter length of an amino acid sequence and an excellent activity in reducing blood sugar, and thus, can reduce the cost for producing the blood sugar reducing polypeptide while still providing similar drug effects to reduce the economic burden of the patients; secondly, the polypeptides of the present invention have a shorter amino acid sequence and have a lower molecular weight, which can be absorbed more easily after being administered to a diabetic patient, and thus, can increase its bioavailability and is superior for clinical treatment; and thirdly, each polypeptide of the present invention has a different length and different constituent of amino acids, and thus, can provide more flexible treating approaches based on the difference (such as the gender, age, symptom, disease condition, and response to the medicament) of each patient.

The polypeptide of the present invention can be obtained by plant extraction, artificial synthesis, gene recombination technique, or a combination thereof The artificial synthesis herein means that, depending on the desired polypeptide, amino acids can be linked in sequence by a manual method, including chemical synthesis methods or a method using a peptide synthesizer that applies the principle of chemical synthesis. Accordingly, the artificial synthesis method generally has the following advantages: changing the primary structure of a polypeptide easily during the synthesis process, adding a particular amino acid conveniently, and modifying the terminal of a polypeptide expediently.

The chemical synthesis methods that can be used to synthesize the polypeptide of the present invention can be divided into a solid phase synthesis method and a liquid phase synthesis method. Generally, the liquid phase synthesis method has to carry out an extraction operation after every linkage step of each amino acid. In addition, a chromatographic purification step is also needed since the peptide intermediates from the extraction are usually mixtures. In other words, using the liquid phase synthesis method to synthesize polypeptides involves the complicated extraction and chromatographic purification steps to obtain products with high purity.

Unlike the liquid phase synthesis method, the solid phase synthesis method is performed in quite a different way. The linkage reaction of amino acids occurs on the solid polymer particle (or a polymer support) in a solvent. In this method, the N-terminal amino acid of a desired polypeptide is first covalently linked to a polymer particle, and then other amino acids are linked in sequence with a specific linkage method. Eventually, the polypeptide is completed. Because the polymer particle is not dissolved in the solvent, the polymer particle (and the desired polypeptide connected to the polymer particle) can be separated from the reaction reagents and side products by a washing and filtering operation after the synthesis process. That is, only one purification step is required at the end of the whole synthesis process in the solid phase synthesis method. Hence, unlike the liquid phase synthesis method, the solid phase synthesis method is relatively convenient and can reduce synthesis time significantly, and thus, it is more advantageous in terms of the synthesis of long-chain polypeptides.

Presently, many kinds of apparatuses for synthesizing polypeptides automatically have been developed, for instance, solid phase peptide synthesizers, liquid phase peptide synthesizers, microwave peptide synthesizers, etc. They all can be opted for synthesizing the polypeptide of the present invention depending on the requirements.

The polypeptide of the present invention also can be synthesized by the gene recombination technique. Herein, an expression vector containing a polynucleotide encoding the polypeptide of the present invention is transformed in a host cell, and the polynucleotide is then expressed to produce the polypeptide of the present invention. The host cell can be Escherichia coli or yeast, and the expression vector can be selected from common vectors available from the market, for example, pQStrep2, pQStrep4, pGEX-6P1, pQTEV, etc.

Moreover, the polypeptide of the present invention also can be obtained from plant extracts. There are several polypeptides capable of modulating blood sugar that can be obtained from the extracts of plants from the cucumber family, such as bitter melon, kakorot, cucumber, pumpkin, gourd, watermelon, snake gourd seed, snake gourd root, and combinations thereof. It has been proven by protein electrophoresis that the polypeptides that are able to modulate blood sugar in the extracts of the plants from the cucumber family all belong to homologous polypeptides. Nonetheless, the polypeptide of the present invention also can be obtained from plants other than those from the cucumber family, such as *Zinnia elegans, Medicago truncatula*, grape, grapefruit, *Sambucus nigra, Arabidopsis thaliana*, rice, and combinations thereof. That is, the source of the polypeptide of the present invention is not limited to the plants from the cucumber family.

For example, the plant extract from bitter melon can be acquired by the following steps. Thereafter, the polypeptide of the present invention can be obtained by purifying the plant extract (for instance, using protein electrophoresis or chromatographic purification). First, a bitter melon is macerated in a solvent to obtain a crude suspension, wherein the solvent can be a phosphate buffer solution, a citrate buffer solution, water, etc. The bitter melon can be disintegrated by a blender or a grinder. Particles in the crude suspension are removed from the liquid phase by a centrifuge at a speed of 12,000 rpm to 15,000 rpm, and then a resultant supernatant is filtered using a filter with a pore size of 0.1 µm to 0.5 µm. A resultant filtrate is then passed through a membrane filter with a 30 kDa cut-off. Eventually, a resultant filtrate is collected to obtain a water-soluble bitter melon extract containing the polypeptide of the present invention. The membrane filter can be selected from conventional membrane filter products, such as AMICON® membrane filter, MILLIPORE® membrane filter, etc. Then, the desired polypeptide can be isolated by using a purification method, such as protein electrophoresis or chromatographic purification. The obtained polypeptide can optionally be digested by a specific protease to obtain a desired polypeptide segment. Herein, there are no specific limitations to the protease, for example, it can be but not limited to serine protease, threonine protease, cysteine protease, etc. Finally, a preservative (e.g., sodium benzoate, salicylic acid, etc.) can be added optionally. The polypeptide is stored at −80° C.

In using protein electrophoresis to isolate the polypeptide of the present invention, two-dimensional gel electrophoresis can be used specifically to isolate the polypeptide. First, the above resultant water-soluble bitter melon extract is subjected to protein precipitation, and the protein precipitate is then subjected to one-dimensional iso-electric focusing (IEF). On the second day, a SDS-PAGE (sodium dodecyl sulfate-polyacrylamide gel electrophoresis) gel is prepared, injected into a gel slot, and flattened by using ethanol. After twenty minutes, the ethanol is poured out from the gel slot, and the gel strip treated by the IEF and a protein molecular weight marker is injected into a sample well, respectively. Electrophoresis is then carried out by using an electric current at 110 volts. Electrophoresis ends when the dye moves to the bottom of the gel. The gel is then removed from the gel slot and is stained with a stain reagent. Then, the stain reagent on the gel is removed by using a wash buffer, and the gel is decolorized by using a destaining buffer. Finally, a protein band at the position of the iso-electric point between 9 to 10, and of the molecular weight of 7 kDa to 10 kDa on the gel is cut and collected, and then, the polypeptide of the present invention is obtained.

Moreover, the polypeptide of the present invention can also be obtained by a combination of the aforesaid methods. For example, a fragment of the desired polypeptide can be first acquired by gene recombination or plant extraction, and then the complete polypeptide can be obtained by artificial synthesis.

The polypeptide of the present invention can be used to produce a medication for reducing blood sugar. Hence, the present invention also provides a pharmaceutical composition for reducing blood sugar, reducing glycated hemoglobin, and ameliorating hepato-renal disorders caused by diabetes, comprising an effective amount of the polypeptide of the present invention and a pharmaceutically acceptable carrier. The pharmaceutical composition of the present invention can be used in both veterinary and human medicine, and it can be in any suitable form and can be applied by any suitable manner without particular limits. For example, to prevent the polypeptide from being degrading by enzymes in the alimentary canal, the pharmaceutical composition of the present invention can be administrated by subcutaneous injection or intravenous injection, and is brought to a released position directly by the blood. When the pharmaceutical composition of the present invention is administrated by oral administration, the pharmaceutical composition may contain an absorbance-retarded reagent to protect itself from the stomach acids and enzymes in the front half segment of the small intestine.

As for a medicament suitable for subcutaneous injection or intravenous injection, the pharmaceutical composition of the present invention can comprise one or more additives, such as an isotonic reagent, a saline buffer solution (such as a phosphate buffer solution or a citrate buffer solution), a solubilizer, an emulsifier, and other carriers, to produce an intravenous injection, an emulsion intravenous injection, a powder injection, a suspension injection, a powder-suspension injection, etc.

In terms of manufacturing a medicament suitable for oral administration, the pharmaceutical composition of the present invention can comprise a pharmaceutically acceptable carrier which has no adverse influence on the activity of the polypeptide of the present invention, such as solvents, oily solvents, thinners, stabilizers, absorption delaying agents, disintegrants, emulsifiers, antioxidants, binders, lubricants, moisture absorbents, etc. The pharmaceutical composition can be prepared in a form suitable for oral administration by any suitable approach, such as a tablet, a capsule, a granule, powder, a fluid extract, a solution, syrup, a suspension, an emulsion, a tincture, etc.

Optionally, other additives, such as a flavoring agent, a toner, a coloring agent, etc., can be added to the pharmaceutical composition of the present invention to enhance the taste and visual appeal of the composition. A suitable amount of a preservative, a conservative, an antiseptic, an anti-fungus reagent, etc., also can be added to improve the storability of the resultant medicament. The pharmaceutical composition may optionally comprise one or more other active components to enhance the effect of the medicament or increase the flexibility for the formulation. For example, one or more active components, such as insulin, α-glucosidase inhibitors, insulin sensitizers, and other active components, can be incorporated into the pharmaceutical composition of the present invention, as long as the other active components have no adverse effect on the polypeptide of the present invention.

When the pharmaceutical composition containing the polypeptide of the present invention is used to reduce the blood sugar of humans or animals, depending on the requirements of the subject, the pharmaceutical composition of the present invention can be applied with various administration frequencies, such as once a day, several times a day, etc. For example, when applied to the human body for treating diabetes by oral administration, the dose of the pharmaceutical composition is about 10 mg/kg-body weight to about 50 mg/kg-body weight per day, based on the amount of the polypeptide of the present invention. If the injection administration is applied, the daily effective dosage of the pharmaceutical composition for reducing blood sugar is 1 nmole/kg-body weight to 5 nmole/kg-body weight., wherein the unit "mg/kg-body weight" or "nmole/kg-body weight" means the dosage required per kg-body weight. However, for patients with acute conditions, the dosage can be increased to several times or several tens of times, depending on practical requirements.

The present invention also provides an isolated nucleic acid molecule encoding the polypeptide of the present invention. The polynucleotide can be obtained by a conventional clone method. For instance, a genomic deoxyribonucleic acid can be first extracted from a plant cell, and is then used as a template for a polymerase chain reaction. After the polymerase chain reaction is completed, a product is purified to provide the isolated polynucleotide of the present invention.

The present invention yet provides a method for reducing blood sugar, reducing glycated hemoglobin, and ameliorating hepato-renal disorders caused by diabetes in a subject, comprising administrating the polypeptide of the present invention to the subject. The polypeptide can be administrated as any suitable form, such as a pharmaceutical composition. The dosage form and dosage amount of the pharmaceutical composition are as described above. With the blood sugar-reducing activity of the polypeptide of the present invention, the method of the present invention is especially useful for treating diabetes.

The present invention will be further illustrated in details with specific examples as follows. However, the following examples are provided only for illustrating the present invention, and the scope of the present invention is not limited thereby.

Materials

Preparation Example (A) Polypeptides: polypeptides with amino acid sequences of SEQ ID NO:1 to SEQ ID NO:364 as described in the appended sequence list were produced by the solid phase synthesis method.

(B) Experimental subjects: three strains of mice, BALB/c (the metabolism of blood sugar is normal), STZ-induced (streptozotocin-induced type I diabetes), and ob/ob (spontaneous type II diabetes), were used to conduct experiments, and they were provided by the National Laboratory Animal Center, Taiwan.

Example 1

Molecular Docking Analysis

The molecular docking analysis was conducted by the following method: the PDB files of insulin receptor (PDB code is 2DTG) and insulin receptor binding protein (i.e., IRBP-1-68 polypeptide having the amino acid sequence of SEQ ID NO:1; PDB code is 1VBW) were obtained from the Protein Data Bank website. Then, a molecular docking software (AutoDock, version 3.05 and 4.0) and grid-based docking programs were used to conduct molecular docking analysis, thereby, evaluating the molecular interaction energy (including Van der Waals force, repulsion energy, hydrogen bond interaction energy, the Coulomb electrostatic energy, and internal steric energy) between ligands (i.e., IRBP-1-68 (SEQ ID NO:1)) and insulin receptors. The analysis result was shown in FIG. 1, showing that IRBP-1-68 (SEQ ID NO:1) (the block area in the center of FIG. 1) can bind to insulin receptors.

Example 2

Insulin Receptor Autophosphorylation Assay

It has been known that when a ligand such as insulin combines with an insulin receptor in a cell, it will result in the autophosphorylation of the insulin receptor, and thereby trigger signal transduction reactions downstream, inducing the transcription and translation of related genes, and triggering glucose transportation to reduce the extracellular glucose concentration or the glucose concentration in the blood and achieve the effect of reducing blood sugar.

Figure 2:
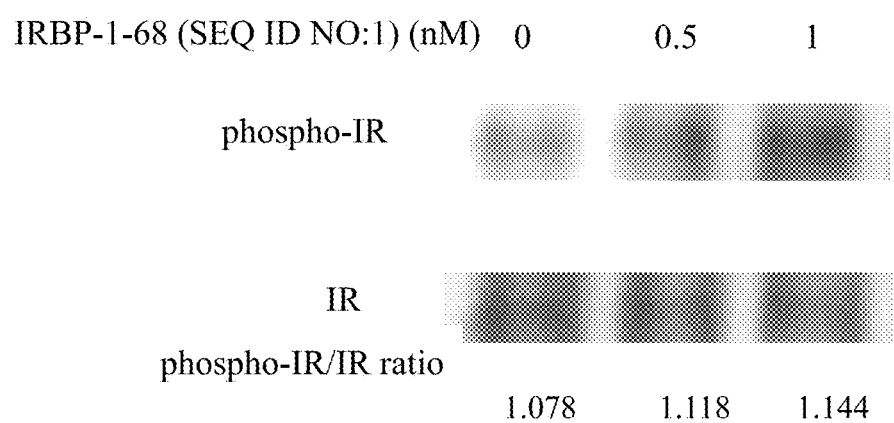
FIG. 2 is an immunoblotting analysis picture showing that IRBP-1-68 (SEQ ID NO:1) promotes the autophosphorylation of insulin receptor.

Therefore, this example conducts an insulin receptor autophosphorylation assay to analyze if IRBP-1-68 polypeptide (SEQ ID NO:1) can result in insulin receptor autophosphorylation, and thereby observe if IRBP-1-68 polypeptide (SEQ ID NO:1) can bind with the insulin receptor. The assay was conducted by the following steps: The human lymphocyte cell line (IM-9) was serum-starved (RPMI medium supplemented with 0.1% BSA) for 16 h and then stimulated with IRBP-1-68 (SEQ ID NO:1) for 15 min at 37° C., and washed with cold PBS. The cells were lysed to obtain about 250 mg of total proteins, while the immunoprecipitation was conducted by the anti-insulin receptor polyclonal antibody (C-19). Then, the protein was adsorbed onto protein G-agarose beads (Gibco-BRL, Gaithersburg, Md.) for 2 h at 4° C., resolved by SDS-PAGE, and transferred to an Immobilon-P membrane by electroblotting. The membrane was incubated with antiphosphotyrosine antibody (4G10) overnight at 4° C. to conduct the immunoblotting analysis. The result was shown in FIG. 2. In FIG. 2, the broader band of the immunoblotting analysis represents a higher protein expression level. In addition, the result of FIG. 2 shows that the ratio of phosphorylated insulin receptor to insulin receptor increased along with the increment of IRBP-1-68 (SEQ ID NO:1) concentration.

As demonstrated in FIG. 2, IRBP-1-68 (SEQ ID NO:1) can induce insulin receptor autophosphorylation, showing it can bind to an insulin receptor.

Example 3

Receptor Binding Assay: IRBP-1-68 (SEQ ID NO:1)

Whole cell receptor binding assays were performed to further confirm if IRBP-1-68 (SEQ ID NO:1) could combine with an insulin receptor.

First, $1.2 \times 10^6$ human lymphocyte cells (IM-9) were separately incubated with insulin (control) or IRBP-1-68 (SEQ ID NO:1) at room temperature for 15 min in 1 ml PBS containing 0.1% bovine serum albumin to conduct competition assays. Then, $^{125}$I-labeled insulin (20,000 cpm/ml) was added thereinto and incubation at 16° C. for 90 min. After incubation, the cells were chilled, centrifuged at 2000 rpm for 10 min at 4° C., and the pellets were washed twice with an ice-cold wash buffer (10 mmol/L Tris and 150 mmol/L NaCl, pH 7.6). The pellet was counted by a gamma counter. The assays were performed at least three times for each polypeptide. The concentration of each polypeptide promoting $^{125}$I-labeled insulin to bind to insulin receptors ($EC_{50}$) was indicated in Table 1, wherein $EC_{50}$ refers to the concentration of a polypeptide that can promote 50% of the $^{125}$I-labeled insulin to bind to insulin receptors. The lower value of $EC_{50}$ represents a stronger effect on promoting the binding.

TABLE 1

| Polypeptide | $EC_{50}$ (nM) |
|---|---|
| Insulin | 7.7 ± 1.11 |
| IRBP-1-68 (SEQ ID NO: 1) | 4.15 ± 1.77 |

As shown in Table 1, insulin and IRBP-1-68 (SEQ ID NO:1) both can effectively promote $^{125}$I-labeled insulin to bind to insulin receptors, wherein the $EC_{50}$ of IRBP-1-68 (SEQ ID NO:1) is 4.15±1.77 nM, lower than that of insulin, showing that IRBP-1-68 (SEQ ID NO:1) can bind with an insulin receptor and has a better effect on promoting insulin to bind to insulin receptors.

Example 4

Glucose Uptake Assay

A key step for modulating blood sugar is that adipose tissue can uptake glucose from the blood and thereby, reduce blood sugar. Accordingly, this example further used 3T3-L1 adipocytes as an assay platform to conduct the glucose uptake assay. 3T3-L1 adipocytes were cultured in 24-well plates, and after a 4.5-h starvation period, the adipocytes were separately incubated in a Krebs ringer bicarbonate buffer (KRB; 118 mM NaCl, 4.7 mM KCl, 1.3 mM $CaCl_2$, 1.2 mM $MgSO_4$, 1.2 mM $Na_2HPO_4$, 2% bovine serum albumin, 0.5 mM glucose, 25 mM $NaHCO_3$, pH 7.4) without insulin (the negative control group), with 1 nM insulin (the control group) and with 1 nM insulin plus IRBP-1-68 (SEQ ID NO:1) (the experimental group) for 30 min, followed by the addition of [3H]-2-deoxy-D-glucose (0.1 μCi/assay) for an additional 10 min. The cells were washed three times with ice-cold phosphate buffered saline (PBS) and then solubilized in 0.1% SDS. The radioactivity in the cells was measured by a scintillation counter, and the result was shown in Table 2.

TABLE 2

| polypeptide | Ratio |
| --- | --- |
| insulin | 2.9 |
| IRBP-1-68 (SEQ ID NO: 1) | 1.79 ± 0.49 |

The radioactivity ratio of insulin shown in Table 2 was referred to Life Sciences 2004; 75:2653-64, which is entirely incorporated hereinto by reference. As shown in Table 2, insulin and IRBP-1-68 (SEQ ID NO:1) both can promote 3T3-L1 adipocytes to uptake glucose. This assay demonstrates that IRBP-1-68 (SEQ ID NO:1) can achieve the effect of reducing blood sugar by promoting adipocytes to uptake glucose.

Example 5

Microarray Analysis

Whole genome scanning was conducted by microarray analysis to discuss the potential mechanism of IRBP-1-68 (SEQ ID NO:1) to promote 3T3-L1 adipocytes to uptake glucose.

Total RNAs were extracted from 3T3-L1 adipocytes which were or were not treated with IRBP-1-68 (SEQ ID NO:1) using RNeasy Mini kit (Qiagen, Valencia, Calif., USA). Total RNA was evaluated using Agilent 2100 bioanalyzer (Agilent Technologies, Santa Clara, Calif., USA). The RNA sample with an RNA integrity number greater than 8.0 was selected. Microarray analysis was performed as described previously (see Cheng, W. Y. et al., 2009, Comprehensive evaluation of a novel nuclear factor-κB inhibitor, quinoclamine, by transcriptomic analysis. Brit. J. Pharmacol. 157(5): 746-756; Cheng, H. M. et al., 2010, Application of bioactivity database of Chinese herbal medicine on the therapeutic prediction, drug development, and safety evaluation. J. Ethnopharmacol. 132 (2): 429-437; and Hsiang, C. Y. et al., 2009, Nuclear factor-κB bioluminescence imaging-guided transcriptomic analysis for the assessment of hoist-biomaterial interaction in vivo. Biomaterials 30 (17): 3042-3049, which are entirely incorporated hereinto by reference).

The number of insulin signal pathway-related or adipocytokine signal pathway-related genes that the expression levels thereof were increased or decreased up to 2 folds were calculated, and the result was shown in Table 3.

TABLE 3

| | number of the genes with changed expression level(total gene number of the pathway) | p value |
| --- | --- | --- |
| insulin signal pathway | 28 (136) | 5.84E−04 |
| adipocytokine signal pathway | 16 (71) | 3.88E−03 |

As shown in Table 3, IRBP-1-68 (SEQ ID NO:1) can regulate the expression level of the insulin signal pathway-related genes in 3T3-L1 adipocytes to promote adipocytes to uptake glucose and achieve the effect of reducing blood sugar.

Example 6

Western Blotting Analysis

The protein expression levels of the insulin signal pathway-related genes were analyzed by the western blotting method.

Figure 3:
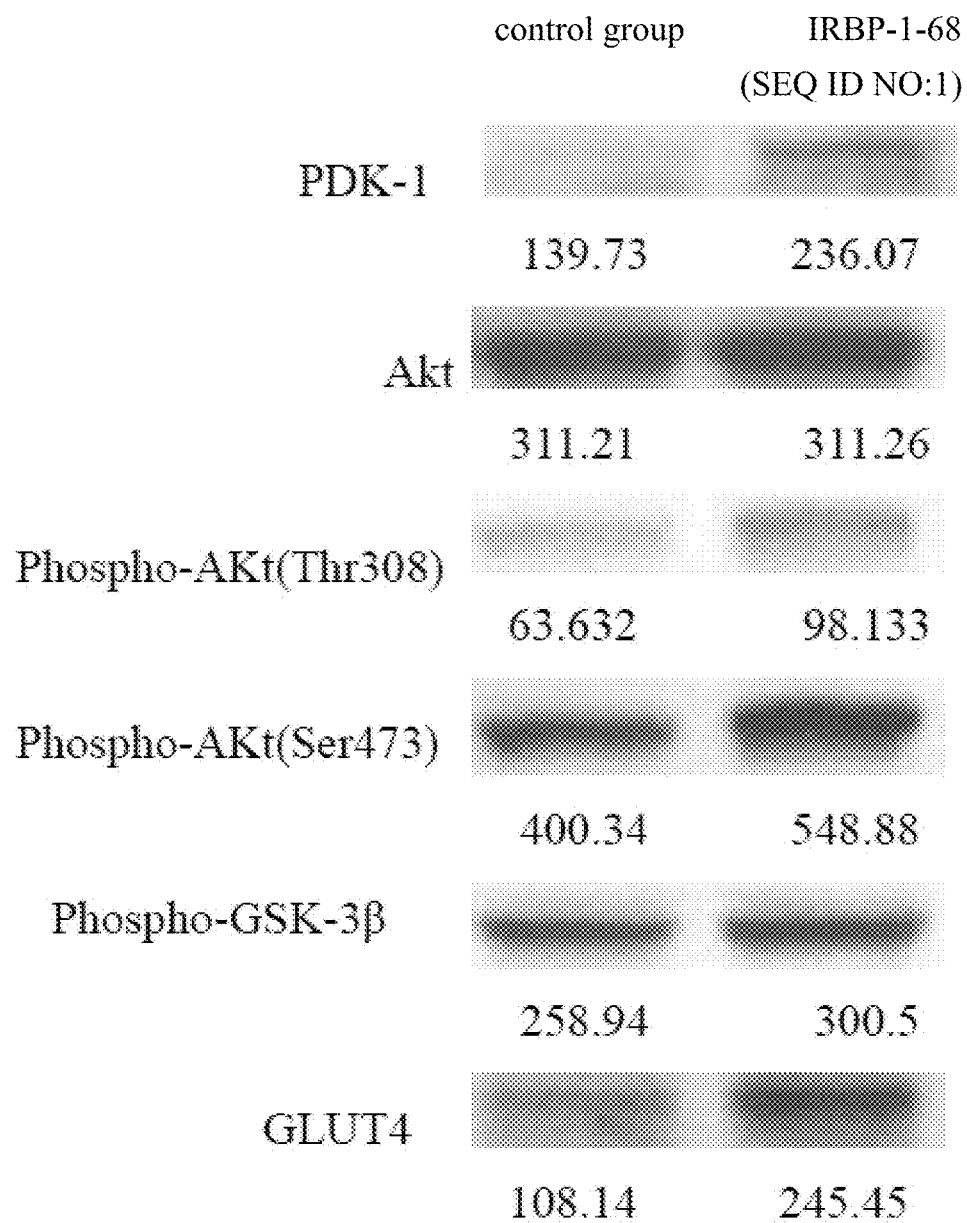
FIG. 3 is a western blotting analysis picture showing that IRBP-1-68 (SEQ ID NO:1) promotes the protein expression of the insulin signal pathway-related genes.

3T3-L1 adipocytes were cultured at 37° C. for 24 hours, treated with IRBP-1-68 (SEQ ID NO:1) for 16 hours, collected using a cell scraper after being washed with ice-cold PBS, and lysed with a 300 μl sample buffer (62.5 mM Tris-HCl, pH 6.8, 2% sodium dodecyl sulfate, 10% glycerol, 50 mM dithiothreitol, 0.1% bromophenol blue). The protein concentration of the cell lysate was determined with a Bradford method (Bio-Rad, Hercules, Calif., USA). The proteins (10 μg) were separated by SDS-PAGE and the protein bands were then transferred electrophoretically to nitrocellulose membranes (Amersham Pharmacia Biotech Inc., Piscataway, N.J., USA). Membranes were blocked in blocking buffer (20 mM Tris-HCl, pH 7.6, 140 mM NaCl, 0.1% Tween-20, 5% skim milk powder) and probed with anti-Akt, anti-phospho-Akt (Ser473), anti-phospho-Akt (Thr308), anti-phospho-PTEN (phosphatase and tensin homolog deleted on Chromosome ten) (Ser380), anti-phospho-GSK-3β (glycogensynthasekinase-3β) (Ser9), anti-phospho-Raf (Ser259), anti-phospho-PDK1 (phosphoinositide-dependent kinase 1) (Ser241) antibodies (Cell Signaling Technology, Beverly, Mass., USA). The result was shown in FIG. 3, wherein the values shown in FIG. 3 represent the intensity of the bands in western blotting analysis. A higher value represents a higher expression level of the target protein.

As shown in FIG. 3, IRBP-1-68 (SEQ ID NO:1) can increase the protein expression levels of the insulin signal pathway-related genes, such as PDK-1, phosphorylated-AKt (Thr 308), phosphorylated-AKt (Ser 473), and glucose transporter 4 (GLUT4). The result of this assay shows that IRBP-1-68 (SEQ ID NO:1) can regulate the expression level of the insulin signal pathway-related genes in 3T3-L1 adipocytes to reduce blood sugar.

Example 7

Immunochemical Analysis

Immunochemical analysis was conducted by the following method: 3T3-L1 adipocytes were cultured and fixed on a cover slide, and incubated with a 1:50 diluted mouse monoclonal antibody against GLUT4 (Millipore, Billerica, Mass., USA) at 4° C. overnight. Then, the cells were incubated with biotinylated secondary antibody (Zymed Laboratories, South San Francisco, Calif., USA) at room temperature for 20 min. Then, the slides were incubated with avidin-biotin complex reagent and stained with 3,3'-diaminobenzidine (HISTOSTAIN®-Plus Kit, Zymed Laboratories, South San Francisco, Calif., USA). The result was shown in FIG. 4.

Figure 4:
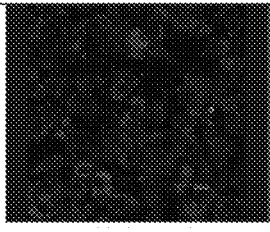
FIG. 4 is an immunohistochemical staining picture showing that IRBP-1-68 (SEQ ID NO:1) promotes 3T3-L1 adipocytes to express GLUT4.

As shown in FIG. 4, the result of the immunochemical staining of 3T3-L1 adipocytes also shows that IRBP-1-68 (SEQ ID NO:1) can promote 3T3-L1 adipocytes to express GLUT4. It has been known that GLUT4 is a protein that can transport glucose in adipocytes. Hence, the above assay result shows that IRBP-1-68 (SEQ ID NO:1) can promote adipocytes to transport glucose by increasing the expression level of GLUT4, thereby, achieving the effect of reducing blood sugar.

The assays of Examples 1 to 7 show that IRBP-1-68 (SEQ ID NO:1) can bind with insulin receptors, and can promote adipocytes in uptaking glucose to reduce blood sugar.

Example 8

Receptor Binding Assay: Segmental Amino Acid Sequence of IRBP-1-68 (SEQ ID NO:1)

The receptor binding assay of the polypeptides having the segmental amino acid sequence (SEQ ID NO:2 SEQ ID NO:3 SEQ ID NO:4 SEQ ID NO:5 SEQ ID NO:6 SEQ ID NO:7) shown in Table 4 was conducted by using the same experimental method as described in Example 2. The concentrations ($EC_{50}$) of these polypeptides promoting $^{125}$I-labeled insulin to bind to insulin receptors are shown in Table 4.

As shown in Table 4, all of the polypeptides of the present invention having the segmental amino acid sequence of IRBP-1-68 (i.e., SEQ ID NO:2 to SEQ ID NO:7) have the effect of promoting insulin to bind to insulin receptors, wherein IRBP-1-19 (SEQ ID NO:2), IRBP-50-68 (SEQ ID NO:6), and IRBP-60-68 (SEQ ID NO:7) have a better promoting effect.

The result of this assay shows that when IRBP-1-68 (SEQ ID NO:1) was cut into 19 amino acids (i.e., IRBP-1-19 (SEQ ID NO:2) and IRBP-50-68 (SEQ ID NO:6)) or even 9 amino acids, it still has the effect of binding to insulin receptors. The following experiments were conducted to further analyze IRBP-60-68 (SEQ ID NO:7).

Example 9

Molecular Docking Analysis: A Homologous Polypeptide Derived from the Substitution of a Single Amino Acid in the Amino Acid Sequence of IRBP-60-68 (SEQ ID NO:7)

As shown in Table 5, the polypeptides having the homologous amino acid sequence (SEQ ID NO:8 to SEQ ID NO:178) derived from the substitution of a single amino acid in IRBP-60-68 (SEQ ID NO:7) were produced by the solid phase synthesis method, and the molecular docking analysis was conducted by the same method described in Example 1.

The molecular interaction energy (including Van der Waals force, repulsion energy, hydrogen bond interaction energy, the Coulomb electrostatic energy, and internal steric energy) between polypeptides and insulin receptors was evaluated, wherein the scaled score of 7000 to 8000 was labeled as "+"; the scaled score of 8000 to 9000 was labeled as "++"; the scaled score of 9000 to 10000 was labeled as "+++". Herein, a higher scaled score represents a larger interaction energy between the polypeptide and insulin receptors, indicating a stronger binding action.

TABLE 4

| polypeptide | SEQ ID NO | sequence | $EC_{50}$ (nM) |
|---|---|---|---|
| IRBP-1-19 | SEQ ID NO: 2 | SRCQGKSSWPGLVGSTGAA | 15.34 ± 3.77 |
| IRBP-17-35 | SEQ ID NO: 3 | GAAAKAVIERENPRVR VI | >25 |
| IRBP-34-52 | SEQ ID NO: 4 | VIIKVGSGATKDFRCDRVR | >25 |
| IRBP-45-68 | SEQ ID NO: 5 | DFRCDRVRVWVTERGIVARPPTIG | >25 |
| IRBP-50-68 | SEQ ID NO: 6 | RVRVWVTERGIVARPPTIG | 0.73 ± 0.06 |
| IRBP-60-68 | SEQ ID NO: 7 | IVARPPTIG | 0.77 ± 0.04 |

TABLE 5

| substituting amino acid | original sequence of IRBP-60-68 (SEQ ID NO: 7) | | | | | | | | |
|---|---|---|---|---|---|---|---|---|---|
| | I | V | A | R | P | P | T | I | G |
| R | +++ (SEQ ID NO: 8) | ++ (SEQ ID NO: 9) | ++ (SEQ ID NO: 10) | | ++ (SEQ ID NO: 11) | ++ (SEQ ID NO: 12) | +++ (SEQ ID NO: 13) | + (SEQ ID NO: 14) | +++ (SEQ ID NO: 15) |
| A | + (SEQ ID NO: 16) | + (SEQ ID NO: 17) | | ++ (SEQ ID NO: 18) | ++ (SEQ ID NO: 19) | + (SEQ ID NO: 20) | ++ (SEQ ID NO: 21) | ++ (SEQ ID NO: 22) | ++ (SEQ ID NO: 23) |
| V | ++ (SEQ ID NO: 24) | | ++ (SEQ ID NO: 25) | ++ (SEQ ID NO: 26) | ++ (SEQ ID NO: 27) | ++ (SEQ ID NO: 28) | ++ (SEQ ID NO: 29) | ++ (SEQ ID NO: 30) | ++ (SEQ ID NO: 31) |
| F | ++ (SEQ ID NO: 32) | +++ (SEQ ID NO: 33) | ++ (SEQ ID NO: 34) | ++ (SEQ ID NO: 35) | + (SEQ ID NO: 36) | ++ (SEQ ID NO: 37) | +++ (SEQ ID NO: 38) | ++ (SEQ ID NO: 39) | ++ (SEQ ID NO: 40) |
| P | ++ (SEQ ID NO: 41) | + (SEQ ID NO: 42) | ++ (SEQ ID NO: 43) | + (SEQ ID NO: 44) | | | + (SEQ ID NO: 45) | + (SEQ ID NO: 46) | ++ (SEQ ID NO: 47) |
| M | ++ (SEQ ID NO: 48) | ++ (SEQ ID NO: 49) | ++ (SEQ ID NO: 50) | + (SEQ ID NO: 51) | + (SEQ ID NO: 52) | ++ (SEQ ID NO: 53) | +++ (SEQ ID NO: 54) | ++ (SEQ ID NO: 55) | ++ (SEQ ID NO: 56) |
| I | | +++ (SEQ ID NO: 57) | + (SEQ ID NO: 58) | ++ (SEQ ID NO: 59) | ++ (SEQ ID NO: 60) | ++ (SEQ ID NO: 61) | ++ (SEQ ID NO: 62) | | +++ (SEQ ID NO: 63) |
| L | ++ (SEQ ID NO: 64) | ++ (SEQ ID NO: 65) | ++ (SEQ ID NO: 66) | ++ (SEQ ID NO: 67) | ++ (SEQ ID NO: 68) | ++ (SEQ ID NO: 69) | ++ (SEQ ID NO: 70) | ++ (SEQ ID NO: 71) | ++ (SEQ ID NO: 72) |
| D | ++ (SEQ ID NO: 73) | ++ (SEQ ID NO: 74) | ++ (SEQ ID NO: 75) | + (SEQ ID NO: 76) | ++ (SEQ ID NO: 77) | + (SEQ ID NO: 78) | ++ (SEQ ID NO: 79) | + (SEQ ID NO: 80) | + (SEQ ID NO: 81) |
| E | ++ (SEQ ID NO: 82) | ++ (SEQ ID NO: 83) | ++ (SEQ ID NO: 84) | ++ (SEQ ID NO: 85) | ++ (SEQ ID NO: 86) | + (SEQ ID NO: 87) | ++ (SEQ ID NO: 88) | + (SEQ ID NO: 89) | ++ (SEQ ID NO: 90) |
| K | ++ (SEQ ID NO: 91) | ++ (SEQ ID NO: 92) | ++ (SEQ ID NO: 93) | ++ (SEQ ID NO: 94) | ++ (SEQ ID NO: 95) | ++ (SEQ ID NO: 96) | ++ (SEQ ID NO: 97) | ++ (SEQ ID NO: 98) | ++ (SEQ ID NO: 99) |
| G | + (SEQ ID NO: 100) | ++ (SEQ ID NO: 101) | ++ (SEQ ID NO: 102) | + (SEQ ID NO: 103) | + (SEQ ID NO: 104) | ++ (SEQ ID NO: 105) | ++ (SEQ ID NO: 106) | ++ (SEQ ID NO: 107) | |
| S | + (SEQ ID NO: 108) | ++ (SEQ ID NO: 109) | ++ (SEQ ID NO: 110) | + (SEQ ID NO: 111) | + (SEQ ID NO: 112) | + (SEQ ID NO: 113) | ++ (SEQ ID NO: 114) | ++ (SEQ ID NO: 115) | + (SEQ ID NO: 116) |
| T | ++ (SEQ ID NO: 117) | ++ (SEQ ID NO: 118) | ++ (SEQ ID NO: 119) | + (SEQ ID NO: 120) | +++ (SEQ ID NO: 121) | ++ (SEQ ID NO: 122) | | ++ (SEQ ID NO: 123) | ++ (SEQ ID NO: 124) |
| Y | ++ (SEQ ID NO: 125) | +++ (SEQ ID NO: 126) | ++ (SEQ ID NO: 127) | ++ (SEQ ID NO: 128) | ++ (SEQ ID NO: 129) | ++ (SEQ ID NO: 130) | ++ (SEQ ID NO: 131) | +++ (SEQ ID NO: 132) | ++ (SEQ ID NO: 133) |
| H | ++ (SEQ ID NO: 134) | ++ (SEQ ID NO: 135) | ++ (SEQ ID NO: 136) | ++ (SEQ ID NO: 137) | ++ (SEQ ID NO: 138) | ++ (SEQ ID NO: 139) | ++ (SEQ ID NO: 140) | ++ (SEQ ID NO: 141) | ++ (SEQ ID NO: 142) |
| C | + (SEQ ID NO: 143) | ++ (SEQ ID NO: 144) | ++ (SEQ ID NO: 145) | ++ (SEQ ID NO: 146) | ++ (SEQ ID NO: 147) | ++ (SEQ ID NO: 148) | ++ (SEQ ID NO: 149) | ++ (SEQ ID NO: 150) | ++ (SEQ ID NO: 151) |
| N | ++ (SEQ ID NO: 152) | ++ (SEQ ID NO: 153) | ++ (SEQ ID NO: 154) | + (SEQ ID NO: 155) | + (SEQ ID NO: 156) | + (SEQ ID NO: 157) | ++ (SEQ ID NO: 158) | ++ (SEQ ID NO: 159) | ++ (SEQ ID NO: 160) |
| Q | ++ (SEQ ID NO: 161) | ++ (SEQ ID NO: 162) | ++ (SEQ ID NO: 163) | + (SEQ ID NO: 164) | +++ (SEQ ID NO: 165) | + (SEQ ID NO: 166) | ++ (SEQ ID NO: 167) | ++ (SEQ ID NO: 168) | ++ (SEQ ID NO: 169) |
| W | ++ (SEQ ID NO: 170) | ++ (SEQ ID NO: 171) | ++ (SEQ ID NO: 172) | + (SEQ ID NO: 173) | ++ (SEQ ID NO: 174) | +++ (SEQ ID NO: 175) | ++ (SEQ ID NO: 176) | ++ (SEQ ID NO: 177) | ++

As shown in Table 5, all of the polypeptides having the homologous amino acid sequence (SEQ ID NO:8 to SEQ ID NO:178) derived from the substitution of a single amino acid in IRBP-60-68 (SEQ ID NO:7) have different levels of ability to bind to insulin receptors.

Example 10

Receptor Binding Assay: A Homologous Polypeptide Derived from the Substitution of a Single Amino Acid in the Amino Acid Sequence of IRBP-60-68 (SEQ ID NO:7)

The receptor binding assay of the polypeptide having the amino acid sequence of SEQ ID NO:21 (i.e., a homologous polypeptide derived from the substitution of the threonine in the amino acid sequence of IRBP-60-68 (SEQ ID NO:7) by alanine; hereinafter refers to as "IRBP-MC" (SEQ ID NO:21)) as shown in Table 5 was conducted by using the same experimental method as described in Example 3. The result is shown in Table 6.

TABLE 6

| polypeptide | SEQ ID NO | sequence | EC$_{50}$ (nM) |
|---|---|---|---|
| IRBP-MC | SEQ ID NO: 21 | IVARPPAIG | 0.86 ± 0.05 |

As shown in Table 6, the concentration of IRBP-MC (SEQ ID NO:21) polypeptide derived from the substitution of a single amino acid in IRBP-60-68 (SEQ ID NO:7) promoting $^{125}$I-labeled insulin to bind to insulin receptors is 0.86±0.05 (nM), showing that the homologous polypeptide derived from the substitution of a single amino acid in the amino acid sequence of IRBP-60-68 (SEQ ID NO:7) still has the ability to bind to insulin receptors.

In addition, as shown in Table 7, the homologous polypeptides derived from the substitution of a single amino acid in the amino acid sequence of IRBP-60-68 (SEQ ID NO:7) were further analyzed by the receptor binding assay. Herein, the activity of insulin receptor tyrosine kinase was used as an indicator of the binding activity of the polypeptides and insulin receptors. The higher of the activity of insulin receptor tyrosine kinase represents a stronger binding ability of the polypeptide to the insulin receptor.

The experimental procedure for evaluating the binding ability of the polypeptides by insulin receptor tyrosine kinase is as follows. The polypeptide and insulin receptor were placed in an ice bath for 30 minutes, and then an equal volume of 2× kinase buffer (50 mM HEPES, pH 7.6; 50 mM MgCl$_2$; 200 μM ATP; 200 Mm sodium vanadate; 5 mg/L poly(Glu, Tyr); 50 μCi [γ-32$^P$]ATP/ml) was added thereinto. The sample was placed in an ice bath for 10 minutes. Then, TCA was added thereinto to precipitate the substrate (poly(Glu, Tyr)) on a filter paper. The filter paper was put into a gamma radiation counter, and the activity of insulin receptor tyrosine kinase was calculated from the radiation intensity.

In Table 7, each group of the polypeptides is a polypeptide mixture of the polypeptides obtained from a substitution to a specific amino acid in the amino acid sequence of IRBP-60-68 (SEQ ID NO:7). For example, IRBP-60-68-1@ represents a polypeptide mixture of the polypeptides obtained from the substitution of the first amino acid in the amino acid sequence of IRBP-60-68 (SEQ ID NO:7) by arginine (Arg; R), alanine (Ala; A), valine (Val; V), phenylalanine (Phe; F), proline (Pro; P), methionine (Met; M), isoleucine (Ile; I), leucine (Leu; L); aspartate (Asp; D), glutamate (Glu; E), lysine (Lys; K), glycine (Gly; G), serine (Ser; S), threonine (Thr; T); tyrosine (Tyr; Y), histidine (His; H), cysteine (Cys; C), asparagine (Asn; N), Glutamine (Gln; Q), or Tryptophan (Trp; W), comprising the polypeptides having an amino acid sequence of SEQ ID NO:8, SEQ ID NO:16, SEQ ID NO:24, SEQ ID NO:32, SEQ ID NO:41, SEQ ID NO:48, SEQ ID NO:64, SEQ ID NO:73, SEQ ID NO:82, SEQ ID NO:91, SEQ ID NO:100, SEQ ID NO:108, SEQ ID NO:117, SEQ ID NO:125, SEQ ID NO134, SEQ ID NO:143, SEQ ID NO:152, SEQ ID NO:161, SEQ ID NO:170.

TABLE 7

| polypeptide | sequence | U/ml |
|---|---|---|
| IRBP-60-68-1@ | @VARPPTIG | 53.23 ± 0.10 |
| IRBP-60-68-2@ | I@ARPPTIG | 54.65 ± 0.37 |
| IRBP-60-68-3@ | IV@RPPTIG | 52.66 ± 0.05 |
| IRBP-60-68-4@ | IVA@PPTIG | 52.86 ± 0.30 |
| IRBP-60-68-5@ | IVAR@PTIG | 83.43 ± 0.43 |
| IRBP-60-68-6@ | IVARP@TIG | 53.28 ± 0.55 |
| IRBP-60-68-7@ | IVARPP@IG | 53.80 ± 0.57 |
| IRBP-60-68-8@ | IVARPPT@G | 53.19 ± 0.16 |
| IRBP-60-68-9@ | IVARPPTI@ | 53.04 ± 0.09 |

As shown in Table 7, the polypeptide mixture of the polypeptides obtained from a substitution to a specific amino acid in the amino acid sequence of IRBP-60-68 (SEQ ID NO:7) has the activity of binding to insulin receptors.

Example 11

Receptor Binding Assay: Homologous Polypeptides Derived from the Substitution of Multiple Amino Acids in the Amino Acid Sequence of IRBP-60-68 (SEQ ID NO:7)

As shown in Table 8, the polypeptides having the homologous amino acid sequence derived from the mutation/substitution of multiple amino acids (replacement of 3 to 6 amino acids) in IRBP-60-68 (SEQ ID NO:7) were produced by the solid phase synthesis method, and the receptor binding assay was conducted by the same method described in Example 3. The name, sequence, and assay result of the said homologous polypeptides were shown in Table 8.

TABLE 8

| polypeptide | SEQ ID NO | sequence | $EC_{50}$ (nM) |
|---|---|---|---|
| IRBP-MT | SEQ ID NO: 179 | IVYQVPTIG | 0.77 ± 0.02 |
| IRBP-VV-2 | SEQ ID NO: 180 | IVISVPTIG | 4.98 ± 0.06 |
| IRBP-SN | SEQ ID NO: 181 | IVTRVPVIG | 9.79 ± 0.13 |
| IRBP-AT | SEQ ID NO: 182 | IVVRNPTAG | 9.98 ± 0.06 |
| IRBP-OS | SEQ ID NO: 183 | TVAKTPTIG | 9.93 ± 0.04 |
| IRBP-CM | SEQ ID NO: 184 | LVVSPPRIG | 0.92 ± 0.08 |
| IRBP-VV-1 | SEQ ID NO: 185 | IVSMVPKIG | 0.96 ± 0.13 |
| IRBP-CP | SEQ ID NO: 186 | KVIRVPRIG | 0.84 ± 0.05 |
| IRBP-ZE | SEQ ID NO: 187 | IVIRTPIIT | 4.94 ± 0.15 |
| IRBP-LU | SEQ ID NO: 188 | VVTSVPHIT | 9.70 ± 0.04 |

As shown in Table 8, the polypeptides having the amino acid sequences of SEQ ID NO:179 to SEQ ID NO:188 have the ability to promote insulin to bind to insulin receptors, showing that the homologous polypeptides having the homologous amino acid sequence derived from the substitution of 3 to 6 amino acids in IRBP-60-68 (SEQ ID NO:7) still have an effect of promoting insulin to bind to insulin receptors, wherein IRBP-MT (SEQ ID NO:179), IRBP-CM (SEQ ID NO:184), IRBP-VV-1 (SEQ ID NO:185), and IRBP-CP (SEQ ID NO:186) have a better promoting effect.

Example 12

Receptor Binding Assay: Homologous Polypeptides Derived from the Substitution of Multiple Amino Acids in the Amino Acid Sequence of IRBP-60-68 (SEQ ID NO:7)

By the method as described in Example 1, four polypeptides (having the amino acid sequences of SEQ ID NO:190 to SEQ ID NO:193; hereinafter referred to as IRBP-9A to IRBP-9D) having 9 amino acids in length and having a better binding ability to insulin receptors were screened by using a molecular docking software to conduct molecular docking analysis.

These polypeptides have a general sequence formula of RYKYQX1X2YI (SEQ ID NO:189), wherein $X_1$ is cysteine or tryptophan and $X_2$ is phenylalanine or tryptophan. These polypeptides were analyzed by the receptor binding assay as described in Example 10. The activity of insulin receptor tyrosine kinase was used as an indicator of the binding activity of the polypeptides and insulin receptors. The result is shown in Table 9.

TABLE 9

| polypeptide | SEQ ID NO | sequence | U/ml |
|---|---|---|---|
| insulin | — | — | 61.28 ± 0.53 |
| IRBP-9A | SEQ ID NO: 190 | RYKYQWFYI | 40.34 ± 1.94 |
| IRBP-9B | SEQ ID NO: 191 | RYKYQCFYI | 79.76 ± 5.64 |
| IRBP-9C | SEQ ID NO: 192 | RYKYQWWYI | 44.18 ± 3.61 |
| IRBP-9D | SEQ ID NO: 193 | RYKYQCWYI | 65.95 ± 1.74 |

The result of Table 9 shows that the polypeptides of IRBP-9A to IRBP-9D (SEQ ID NO:190 to SEQ ID NO:193) can bind to insulin receptors. For example, for IRBP-9B (SEQ ID NO:191), the activity of insulin receptor tyrosine kinase can be up to 79.76±5.64 (U/ml).

Example 13

Molecular Docking Analysis: Homologous Polypeptides Derived from the Substitution of a Single Amino Acid in the Amino Acid Sequence of IRBP-9B (SEQ ID NO:191)

As shown in Table 10, the polypeptides having the homologous amino acid sequences (SEQ ID NO:194 to SEQ ID NO:364) derived from the substitution of a single amino acid in IRBP-9B (SEQ ID NO:191) were produced by the solid phase synthesis method. The molecular docking analysis was conducted by the same method described in Example 1 to evaluate the interaction energy (including Van der Waals force, repulsion energy, hydrogen bond interaction energy, the Coulomb electrostatic energy, and internal steric energy) between the ligand (polypeptides) and insulin receptors, wherein the scaled score of 8000 to 10000 was labeled as "+"; the scaled score of 10000 to 12000 was labeled as "++"; the scaled score of 12000 to 14000 was labeled as "+++". Herein, a higher scaled score represents a larger interaction energy between the polypeptides and insulin receptors, indicating a stronger binding action.

TABLE 10

| substituting amino acid | original sequence of IRBP-9B (SEQ ID NO: 191) | | | | | | | | |
|---|---|---|---|---|---|---|---|---|---|
| | R | Y | K | Y | Q | C | F | Y | I |
| R | | ++ (SEQ ID NO: 194) | + (SEQ ID NO: 195) | + (SEQ ID NO: 196) | ++ (SEQ ID NO: 197) | + (SEQ ID NO: 198) | ++ (SEQ ID NO: 199) | + (SEQ ID NO: 200) | + (SEQ ID NO: 201) |
| A | ++ (SEQ ID NO: 202) | + (SEQ ID NO: 203) | + (SEQ ID NO: 204) | + (SEQ ID NO: 205) | + (SEQ ID NO: 206) | + (SEQ ID NO: 207) | ++ (SEQ ID NO: 208) | ++ (SEQ ID NO: 209) | + (SEQ ID NO: 210) |
| V | + (SEQ ID NO: 211) | + (SEQ ID NO: 212) | + (SEQ ID NO: 213) | + (SEQ ID NO: 214) | ++ (SEQ ID NO: 215) | ++ (SEQ ID NO: 216) | ++ (SEQ ID NO: 217) | + (SEQ ID NO: 218) | + (SEQ ID NO: 219) |
| F | + (SEQ ID NO: 220) | ++ (SEQ ID NO: 221) | + (SEQ ID NO: 222) | ++ (SEQ ID NO: 223) | + (SEQ ID NO: 224) | ++ (SEQ ID NO: 225) | | ++ (SEQ ID NO: 226) | + (SEQ ID NO: 227) |
| P | + (SEQ ID NO: 228) | + (SEQ ID NO: 229) | + (SEQ ID NO: 230) | + (SEQ ID NO: 231) | + (SEQ ID NO: 232) | + (SEQ ID NO: 233) | + (SEQ ID NO: 234) | + (SEQ ID NO: 235) | + (SEQ ID NO: 236) |
| M | + (SEQ ID NO: 237) | + (SEQ ID NO: 238) | + (SEQ ID NO: 239) | + (SEQ ID NO: 240) | + (SEQ ID NO: 241) | + (SEQ ID NO: 242) | + (SEQ ID NO: 243) | ++ (SEQ ID NO: 244) | + (SEQ ID NO: 245) |
| I | + (SEQ ID NO: 246) | ++ (SEQ ID NO: 247) | + (SEQ ID NO: 248) | ++ (SEQ ID NO: 249) | ++ (SEQ ID NO: 250) | +++ (SEQ ID NO: 251) | ++ (SEQ ID NO: 252) | + (SEQ ID NO: 253) | |
| L | + (SEQ ID NO: 254) | + (SEQ ID NO: 255) | + (SEQ ID NO: 256) | + (SEQ ID NO: 257) | + (SEQ ID NO: 258) | + (SEQ ID NO: 259) | ++ (SEQ ID NO: 260) | ++ (SEQ ID NO: 261) | + (SEQ ID NO: 262) |

TABLE 10-continued

| substituting amino acid | original sequence of IRBP-9B (SEQ ID NO: 191) | | | | | | | | |
|---|---|---|---|---|---|---|---|---|---|
| | R | Y | K | Y | Q | C | F | Y | I |
| D | ++ (SEQ ID NO: 263) | + (SEQ ID NO: 264) | + (SEQ ID NO: 265) | + (SEQ ID NO: 266) | + (SEQ ID NO: 267) | + (SEQ ID NO: 268) | + (SEQ ID NO: 269) | + (SEQ ID NO: 270) | + (SEQ ID NO: 271) |
| E | ++ (SEQ ID NO: 272) | ++ (SEQ ID NO: 273) | ++ (SEQ ID NO: 274) | ++ (SEQ ID NO: 275) | ++ (SEQ ID NO: 276) | + (SEQ ID NO: 277) | ++ (SEQ ID NO: 278) | + (SEQ ID NO: 279) | ++ (SEQ ID NO: 280) |
| K | + (SEQ ID NO: 281) | + (SEQ ID NO: 282) | | + (SEQ ID NO: 283) | ++ (SEQ ID NO: 284) | + (SEQ ID NO: 285) | + (SEQ ID NO: 286) | + (SEQ ID NO: 287) | + (SEQ ID NO: 288) |
| G | + (SEQ ID NO: 289) | + (SEQ ID NO: 290) | + (SEQ ID NO: 291) | + (SEQ ID NO: 292) | + (SEQ ID NO: 293) | + (SEQ ID NO: 294) | + (SEQ ID NO: 295) | ++ (SEQ ID NO: 296) | + (SEQ ID NO: 297) |
| S | ++ (SEQ ID NO: 298) | + (SEQ ID NO: 299) | + (SEQ ID NO: 300) | + (SEQ ID NO: 301) | ++ (SEQ ID NO: 302) | + (SEQ ID NO: 303) | + (SEQ ID NO: 304) | + (SEQ ID NO: 305) | + (SEQ ID NO: 306) |
| T | + (SEQ ID NO: 307) | + (SEQ ID NO: 308) | + (SEQ ID NO: 309) | + (SEQ ID NO: 310) | + (SEQ ID NO: 311) | + (SEQ ID NO: 312) | ++ (SEQ ID NO: 313) | + (SEQ ID NO: 314) | ++ (SEQ ID NO: 315) |
| Y | + (SEQ ID NO: 316) | | + (SEQ ID NO: 317) | | + (SEQ ID NO: 318) | + (SEQ ID NO: 319) | ++ (SEQ ID NO: 320) | | ++ (SEQ ID NO: 321) |
| H | ++ (SEQ ID NO: 322) | + (SEQ ID NO: 323) | + (SEQ ID NO: 324) | + (SEQ ID NO: 325) | + (SEQ ID NO: 326) | + (SEQ ID NO: 327) | + (SEQ ID NO: 328) | ++ (SEQ ID NO: 329) | + (SEQ ID NO: 330) |
| C | + (SEQ ID NO: 331) | + (SEQ ID NO: 332) | + (SEQ ID NO: 333) | + (SEQ ID NO: 334) | ++ (SEQ ID NO: 335) | | + (SEQ ID NO: 336) | ++ (SEQ ID NO: 337) | + (SEQ ID NO: 338) |
| N | ++ (SEQ ID NO: 339) | ++ (SEQ ID NO: 340) | ++ (SEQ ID NO: 341) | + (SEQ ID NO: 342) | + (SEQ ID NO: 343) | + (SEQ ID NO: 344) | + (SEQ ID NO: 345) | + (SEQ ID NO: 346) | + (SEQ ID NO: 347) |
| Q | ++ (SEQ ID NO: 348) | ++ (SEQ ID NO: 349) | + (SEQ ID NO: 350) | ++ (SEQ ID NO: 351) | | + (SEQ ID NO: 352) | + (SEQ ID NO: 353) | + (SEQ ID NO: 354) | + (SEQ ID NO: 355) |
| W | + (SEQ ID NO: 356) | ++ (SEQ ID NO: 357) | + (SEQ ID NO: 358) | ++ (SEQ ID NO: 359) | + (SEQ ID NO: 360) | ++ (SEQ ID NO: 361) | ++ (SEQ ID NO: 362) | ++ (SEQ ID NO: 363) | ++ (SEQ ID NO: 364) |

As shown in Table 10, all of the polypeptides having the homologous amino acid sequences (SEQ ID NO:194 to SEQ ID NO:364) derived from the substitution of a single amino acid in IRBP-9B (SEQ ID NO:191) have different levels of ability to bind to insulin receptors.

Example 14

Blood Sugar Reducing Assay

IRBP-1-68 (SEQ ID NO:1), the polypeptides having the segmental amino acid sequences of IRBP, and the polypeptides derived from the substitution of multiple amino acids in the segmental amino acid sequences were analyzed by a blood sugar reducing assay. First, three mice (BALB/c) which are normal in blood sugar metabolism were starved for 18 hours, while three diabetic mice (STZ-induced or ob/ob) were starved for 4 hours. The polypeptides (100 µl, 2.5×10$^{-9}$ mole/kg body weight) as shown in Table 11 were administrated to each mouse in an experimental group by intraperitoneal injection. Each mouse in the control group was administrated with 100 µl water. After 15 minutes, a glucose solution (4 g/kg body weight) was administrated to normal mice (BALB/c) by intraperitoneal injection, and a glucose solution (1 g/kg body weight) was administrated to diabetic mice (STZ-induced or ob/ob) to rapidly increase the blood sugar value of the mice. After 150 minutes, blood samples were collected from the mouse tails, while the blood sugar value was measured by a glucometer (ACCU-CHEK Advantage, Roche, Germany). The blood sugar values of the mice in the experimental group and control group were compared and analyzed.

TABLE 11

| polypeptide | SEQ ID NO | Mice | blood sugar inhibition ratio (%) |
|---|---|---|---|
| IRBP-1-68 | SEQ ID NO: 1 | BALB/c | 68.9 ± 0.9* |
| IRBP-50-68 | SEQ ID NO: 6 | BALB/c | 66.3 ± 3.9* |
| IRBP-60-68 | SEQ ID NO: 7 | BALB/c | 67.0 ± 5.4* |
| IRBP-9B | SEQ ID NO: 191 | BALB/c | 61.0 ± 2.5* |
| IRBP-1-68 | SEQ ID NO: 1 | STZ-induced | 37.3 ± 3.8 |
| IRBP-50-68 | SEQ ID NO: 6 | STZ-induced | 36.0 ± 7.1* |
| IRBP-60-68 | SEQ ID NO: 7 | STZ-induced | 66.5 ± 7.8* |
| IRBP-9A | SEQ ID NO: 190 | STZ-induced | 34.2 ± 13.6 |
| IRBP-9B | SEQ ID NO: 191 | STZ-induced | 47.5 ± 5.0 |
| IRBP-9C | SEQ ID NO: 192 | STZ-induced | 22.6 ± 9.0 |
| IRBP-9D | SEQ ID NO: 193 | STZ-induced | 45.0 ± 7.9 |
| IRBP-1-68 | SEQ ID NO: 1 | ob/ob | 55.6 ± 12.9* |
| IRBP-50-68 | SEQ ID NO: 6 | ob/ob | 51.0 ± 14.2* |
| IRBP-60-68 | SEQ ID NO: 7 | db/db | 33.1 ± 11.5* |

(Data were analyzed by Student's t-test, *p < 0.05)

As shown in Table 11, 2.5×10$^{-9}$ mole/kg body weight of IRBP-1-68 (SEQ ID NO:1) or the homologous polypeptides derived from the same can effectively reduce the blood sugar values of both normal mice and diabetic mice. In the group of BALB/c mice, the polypeptides of IRBP-1-68 (SEQ ID NO:1), IRBP-50-68 (SEQ ID NO:6), IRBP-60-68 (SEQ ID NO:7), and IRBP-9B (SEQ ID NO:191) can achieve a blood inhibition ratio of about 61% to 70%. In the group of STZ-induced mice, the polypeptides of IRBP-1-68 (SEQ ID NO:1), IRBP-50-68 (SEQ ID NO:6), IRBP-60-68 (SEQ ID NO:7), IRBP-9A (SEQ ID NO:190), IRBP-9B (SEQ ID NO:191), IRBP-9C (SEQ ID NO:192), and IRBP-9D (SEQ ID NO:193) can achieve a blood inhibition ratio of about 22% to 67%. In the group of ob/ob or db/db mice, the polypeptides of IRBP-1-68 (SEQ ID NO:1), IRBP-50-68 (SEQ ID NO:6), and IRBP-60-68 (SEQ ID NO:7) can achieve a blood inhibition ratio of about 33% to 55%. The above results show that all of IRBP-1-68 (SEQ ID NO:1), the polypeptides having the segmental amino acid sequences of IRBP-1-68 (SEQ ID NO:1), and the polypeptides derived from the substitution of multiple amino acids in the segmental amino acid sequences have the effect of reducing blood sugar.

Example 15

Glycated Hemoglobin Value Assay

Glycated hemoglobin value (HbAlc) is the concentration of glucose attached on red blood cells in the blood of an organism. In general, a higher concentration of blood sugar reflects a higher glycated hemoglobin value, while the glycated hemoglobin value is a standard for evaluating the effect of a medicament on treating diabetes. Therefore, in this example, the effect of the polypeptide on controlling the blood sugar values of the mice were evaluated by measuring the glycated hemoglobin value.

As shown in Table 12, the polypeptides of IRBP-50-68 (SEQ ID NO:6) and IRBP-60-68 (SEQ ID NO:7) were administrated to diabetic mice (STZ-induced). In the experimental group, the polypeptides ($1\times10^{-6}$ mole/kg body weight, 20 μl) were orally administrated to each mouse in the experimental group. In the control group, each mouse was administrated by 20 μl water. The glycated hemoglobin value was measured after 28 days.

TABLE 12

| polypeptide | SEQ ID NO | glycated hemoglobin value (%) |
|---|---|---|
| (control group) | — | 7.55 ± 0.33 |
| IRBP-50-68 | SEQ ID NO: 6 | 5.93 ± 0.55* |
| IRBP-60-68 | SEQ ID NO: 7 | 5.73 ± 0.11*** |

(Data were analyzed by Student's t-test, *p < 0.05, ***p < 0.001)

As shown in Table 12, the polypeptides of the present invention can effectively reduce the glycated hemoglobin value of the diabetic mice, showing that the polypeptides indeed have the effect of reducing blood sugar value of the diabetic mice.

Example 16

Measurement of Liver Index

Because complications such as hepato-renal disorders usually occur in diabetic patients, in this example, the effect of the polypeptides of the present invention on controlling hepato-renal disorders caused by diabetes in mice were evaluated by measuring the liver index.

The polypeptide of IRBP-50-68 (SEQ ID NO:6) was orally administrated to the diabetic mice in the experimental group by the same method as described in Example 14. After 28 days, the liver indexes (GOT and GPT) of these mice were measured to evaluate the effect of the polypeptide on the hepato disorders caused by diabetes in diabetic mice. The result is shown in Table 13.

TABLE 13

| polypeptide | SEQ ID NO | GOT | GPT |
|---|---|---|---|
| (control group) | — | 838.45 ± 33.64 | 202.95 ± 30.10 |
| IRBP-50-68 | SEQ ID NO: 6 | 247.89 ± 97.38*** | 135.72 ± 30.72* |

(Data were analyzed by Student's t-test, *p < 0.05, ***p < 0.001)

As shown in Table 13, the polypeptide of the present invention can effectively reduce the liver indexes (GOT and GPT) of the diabetic mice, showing that the polypeptide can ameliorate hepato disorders caused by diabetes in the diabetic mice by the effect of reducing blood sugar.

Example 17

Measurement of Renal Index

The polypeptides of IRBP-50-68 (SEQ ID NO:6) and IRBP-60-68 (SEQ ID NO:7) were orally administrated to the diabetic mice in the experimental group by the same method as described in Example 14. After 28 days, the kidney indexes (BUN and CRE) in the blood of these mice were measured to evaluate the effects of these polypeptides on the renal disorders caused by diabetes. The result is shown in Table 14.

TABLE 14

| polypeptide | SEQ ID NO | BUN | CRE |
|---|---|---|---|
| (control group) | — | 88.84 ± 11.76 | 0.302 ± 0.06 |
| IRBP-50-68 | SEQ ID NO: 6 | 107.25 ± 42.99 | 0.191 ± 0.12 |
| IRBP-60-68 | SEQ ID NO: 7 | 73.17 ± 29.95 | 0.17 ± 0.04* |

(Data were analyzed by Student's t-test, *p < 0.05)

As shown in Table 14, the polypeptide of the present invention can effectively reduce the kidney indexes (BUN and CRE) of the diabetic mice, showing that the polypeptide can ameliorate renal disorders caused by diabetes in the diabetic mice by the effect of reducing blood sugar.

The above disclosure is related to the detailed technical contents and inventive features thereof People skilled in this field may proceed with a variety of modifications and replacements based on the disclosures and suggestions of the invention as described without departing from the characteristics thereof Nevertheless, although such modifications and replacements are not fully disclosed in the above descriptions, they have substantially been covered in the following claims as appended.

What is claimed is:

1. An isolated polypeptide consisting of the amino acid sequence of RYKYQX1X2YI (SEQ ID NO: 189) or a homologous amino acid sequence derived from the substitution of a single amino acid in SEQ ID NO: 189, wherein X1 is cysteine or tryptophan and X2 is phenylalanine or tryptophan.

2. The polypeptide as claimed in claim 1, which has the amino acid sequence of SEQ ID NO: 189.

3. The polypeptide as claimed in claim 1, wherein X1 is cysteine.

4. The polypeptide as claimed in claim 1, which has the amino acid sequence of RYKYQCFYI (SEQ ID NO: 191) or a homologous amino acid sequence derived from the substitution of a single amino acid in SEQ ID NO: 191, wherein the homologous amino acid sequence is the amino acid sequence selected from the group consisting of SEQ ID NO:194 to SEQ ID NO:364.

5. A vector containing a polynucleotide encoding the polypeptide as claimed in claim 1.

6. A method for at least one of reducing blood sugar, reducing glycated hemoglobin, and ameliorating hepato-renal disorders caused by diabetes in a subject, comprising administering to the subject an effective amount of the polypeptide as claimed in claim 1.

* * * * *